United States Patent
Baltes et al.

(10) Patent No.: US 12,012,607 B2
(45) Date of Patent: Jun. 18, 2024

(54) ENGINEERING WHEAT WITH INCREASED DIETARY FIBER

(71) Applicant: CELLECTIS, Paris (FR)

(72) Inventors: Nicholas Baltes, Maple Grove, MN (US); Javier Gil Humanes, Circle Pines, MN (US)

(73) Assignee: Cellectis, Paris (FR)

( * ) Notice: Subject to any disclaimer, the term of this patent is extended or adjusted under 35 U.S.C. 154(b) by 62 days.

(21) Appl. No.: 17/052,351

(22) PCT Filed: May 2, 2019

(86) PCT No.: PCT/IB2019/053610
§ 371 (c)(1),
(2) Date: Nov. 2, 2020

(87) PCT Pub. No.: WO2019/211796
PCT Pub. Date: Nov. 7, 2019

(65) Prior Publication Data
US 2021/0079412 A1 Mar. 18, 2021

Related U.S. Application Data

(60) Provisional application No. 62/665,643, filed on May 2, 2018.

(51) Int. Cl.
*C12N 15/82* (2006.01)
*C12N 9/16* (2006.01)

(52) U.S. Cl.
CPC .......... *C12N 15/8245* (2013.01); *C12N 9/16* (2013.01); *C12N 15/8262* (2013.01)

(58) Field of Classification Search
None
See application file for complete search history.

(56) References Cited

U.S. PATENT DOCUMENTS 7,812,221 B2 * 10/2010 Regina .................. A23L 29/212
800/278
9,060,533 B2 * 6/2015 Regina ............... C12N 15/8245
9,150,839 B2 * 10/2015 Slade ................. C12N 15/8245
9,834,776 B2 * 12/2017 Boerjan .................... C12N 9/16
2012/0114770 A1 5/2012 Regina et al.
2013/0090462 A1 4/2013 Slade et al.

FOREIGN PATENT DOCUMENTS

| JP | 2015504301 A | 2/2015 |
| JP | 2016514480 A | 5/2016 |
| WO | 2005/001098 A1 | 1/2005 |
| WO | 2013063653 A1 | 5/2013 |
| WO | 2014/165612 A2 | 10/2014 |

OTHER PUBLICATIONS

Botticella et al, 2011, BMC Plant Biology, 11:1-14.*
Wang et al, 2014, Nature Biotechnology, 32:947-952.*
Khan, et al., "Use of TALEs and TALEN Technology for Genetic Improvement of Plants", Springer Science+Business Media, New York, Aug. 11, 2016.
"International Search Report and Written Opinion for PCT/IB2019/053610,", dated Nov. 7, 2019.
Gaj, et al., "ZFN, TALEN, and CRISPR/Cas-based methods for genome engineering", NIH Public Access Author Manuscript, vol. 31. No. 7, May 9, 2013 (May 9, 2013), pp. 1-20, XP55465031, DOI: 10.1016/j.tibtech.2013.04.004 the whole document.
Japanese Final Office Action dated Jun. 7, 2022, for corresponding Japanese patent application No. P2020-561705.
Malahn et al., "Plant genome editing with TALEN and CRISPR," Cell Biosci. 7:21 (Apr. 24, 2017).
Canadian Office Action dated Nov. 18, 2022, for corresponding Canadian patent application No. 3,099,102.
Chinese Office Action dated May 8, 2023, for corresponding Chinese patent application No. 201980042136X.
Botticella et al., "Triticum aestivum sbeiia ene fot starch branching enzyme IIa", EMBL, HE591389 (Aug. 22, 2012).

* cited by examiner

*Primary Examiner* — Jason Deveau Rosen
(74) *Attorney, Agent, or Firm* — Dicke, Billig & Czaja, PLLC

(57) ABSTRACT

Materials and methods are provided for making plants (e.g., *Triticum* varieties) with increased levels of dietary fiber, such as by making TALE nuclease-induced mutations in alleles encoding starch branching enzyme IIa (SBEIIa) and starch branching enzyme IIb (SBEIIb).

29 Claims, 14 Drawing Sheets

Specification includes a Sequence Listing.

FIG. 1

>SBEIIa-A Exon 2
GCGCCGTCCTGAGCCGCCGCGGCCTCTCCAGGAAGGTCCTGGTGCCTGACGGTGAGAGCGACGACTTGGCAAGTC
CGGCGCAACCTGAAGAATTACAG (SEQ ID NO:11890)

>SBEIIa-A Exon 3
ATACCTGAAGACATCGAGGAGCAAACGGCTGAAGTAAACATGACAGGGGGACTGCAGAAAAACTTGAATCTTCAGA
ACCGACTCAAGGCATTGTGAAACAATCACTGATGGTGTAACCAAAGGAGTTAAGGAACTAGTCGTGGGGGAGAAAC
CGCGAGTTGTCCCAAAACCAGGAGATGGGCAGAGAATATACGAGATTGACCCAACGCTGAAAGATTTTCGGAGCCAT
CTTGACTACCG (SEQ ID NO:11891)

>SBEIIa-B Exon 2
GCGCCGTCCTGAGCCGCCGCGGCCTCTCCAGGAAGGTCCTGGTGCCTGACGGTGAGAGCGACGACTTGGCGGGCCA
CTCCAGCGCAACCCGAAGAATTACAG (SEQ ID NO:11892)

>SBEIIa-B Exon 3
ATACCTGAAGATATCGAGGAGCAAACGGCTGAAGTGAACATGACAGGGGGACTGCAGAGAAACTTCAATATTCAGA
ACCGACTCAGGGCATTGTGAAACAATCACTGATGGTGTAACCAAAGGAGTTAAGGAACTAGTCGTGGGGGAGAAAC
CGCGAGTTGTCCCAAAACCAGGAGATGGGCAGAGAATATACGAGATTGACCCAACGCTGAAAGATTTTCGGAGCCAT
CTTGACTACCG (SEQ ID NO:11893)

>SBEIIa-D Exon 2
GCGCCGTCCTGAGCCGCCGCGGCCTCTCCAGGAAGGTCCTGGTGCCTGACGGTGAGAGCGACGACTTGGCAAGTC
CGGCGCAACCTGAAGAATTACAG (SEQ ID NO:11894)

>SBEIIa-D Exon 3
ATACCTGAAGATATCGAGGAGCAAACGGCGGAAGTGAACATGACAGGGGGACTGCAGAGAAACTTCAATCTTCAGA
ACCGACTCAGGGCATTGTGAAACAATCACTGATGGTGTAACCAAAGGAGTTAAGGAACTAGTCGTGGGGGAGAAAC
CGCGAGTTGTCCCAAAACCAGGAGATGGGCAGAAAATATACGAGATTGACCCAACACTGAAAGATTTTCGGAGCCAT
CTTGACTACCG (SEQ ID NO:11895)

SBEIIa_T1

SBEIIa-A: TATACGAGATTGACCCAAACGCTGAAAGATTTTCGGAGCCATCTTGACTA (SEQ ID NO:11896)
SBEIIa-B: TATACGAGATTGACCCAAACGCTGAAAGATTTTCGGAGCCATCTTGACTA (SEQ ID NO:11896)
SBEIIa-D: TATACGAGATTGACCCAACaCTGAAAGATTTTCGGAGCCATCTTGACTA (SEQ ID NO:11897)

SBEIIa_T2

SBEIIa-A: TTCAGAACCGACTCAaGGCATTGTGGAAACAATCACTGATGGTGTAACCA (SEQ ID NO:11898)
SBEIIa-B: TTCAGAACCGACTCAGGGCATTGTGGAAACAATCACTGATGGTGTAACCA (SEQ

FIG. 4

Plant Ta125-2

SBEIIa-A

WT:  GTCATCCTTGCATTGCAGGCGCCGTCCTGAGCCGGCGGCCTCTCCAGGG--AAGTCCTGGTGCCTGAC
     GGTGAGAGCGACGACTTGGCAAGTCCGGCGCA (SEQ ID NO:11908)

+2:  GTCATCCTTGCATTGCAGGCGCCGTCCTGAGCCGGCGGCCTCTCCAGGGgAAGGTCCTGGTGCCTGAC
     GGTGAGAGCGACGACTTGGCAAGTCCGGCGCA (SEQ ID NO:11909)

-23: GTCATCCTTGCATTGCAGGCGCCGTCCTGAGCCGGCCT-----------------GAC
     GGTGAGAGCGACGACTTGGCAAGTCCGGCGCA (SEQ ID NO:11910)

SBEIIa-B

WT:  CTCATCCTTGCATTTGCAGGCGCCGTCCTGAGCCGGCGGCCTCTCCAGGGAAGGTCCTGGTGCCTGACG
     GTGAGAGCGACGACTTGGGCGGCCACTCCAGCGCA (SEQ ID NO:11911)

-4:  CTCATCCTTGCATTTGCAGGCGCCGTCCTGAGCCGGCGGCCTCTCCA----AGGTCCTGGTGCCTGACG
     GTGAGAGCGACGACTTGGGCGGCCACTCCAGCGCA (SEQ ID NO:11912)

-20: CTCATCCTTGCATTTGCAGGCGCCGTCCTGAGCCGGCGGC--------------------TGCCTGACG
     GTGAGAGCGACGACTTGGGCGGCCACTCCAGCGCA (SEQ ID NO:11913)

SBEIIa-D

WT:  GTCATCCTTGCATTTGCAGGCGCCGCCGTCCTGAGCCGGCCTCTCCAGGGAAGTCCTGGTGCCTGAC
     GGCGAGAGCGACGACTTGGCAAGTCCGGCGCA (SEQ ID NO:11914)

-4:  GTCATCCTTGCATTTGCAGGCGCCGCCGTCCTGAGCCGGCCTCTCCA----AGGTCCTGGTGCCTGAC
     GGCGAGAGCGACGACTTGGCAAGTCCGGCGCA (SEQ ID NO:11915)

-12: GTCATCCTTGCATTTGCAGGCGCCGCCGTCCTGAGCCGGCC------------GTCCTGGTGCCTGAC
     GGCGAGAGCGACGACTTGGCAAGTCCGGCGCA (SEQ ID NO:11916)

FIG. 5

Plant Ta128-1

SBEIIa-A

WT: GTCATCCTTGCATTGCAGGCGCCGTTCCTGAGCCGGCCGTCCTGGTGCCTGACGG
TGAGAGCGACGACTTGGCAAGTCCGGCGCA (SEQ ID NO:11908)

SBEIIa-B

WT: CTCATCCTTGCATTTGCAGGCGCGCCGTTCCTGAGCCGGCCGTCCTGGTGCCTGAC
GGTGAGAGCGACGACTTGGCGGCCACTCCAGCGCA (SEQ ID NO:11911)

+1: CTCATCCTTGCATTTGCAGGCGCGCCGTCCTGAGCCGGCCGCTCTCCAgGGGAAGGTCCTGGTGCCTGAC
GGTGAGAGCGACGACTTGGCGGCCACTCCAGCGCA (SEQ ID NO:11917)

-1: CTCATCCTTGCATTTGCAGGCGCGCCGTCCTGAGCCGGCCGCTCTCCA---GGAAGGTCCTGGTGCCTGAC
GGTGAGAGCGACGACTTGGCGGCCACTCCAGCGCA (SEQ ID NO:11918)

SBEIIa-D

WT: GTCATCCTTGCATTTGCAGGCGCCGTCCTGAGCCGGCCGCCTCTCCAGGGAAGGTCCTGGTGCCTG
ACGGCGAGAGCGACGACTTGGCAAGTCCGGGCGCA (SEQ ID NO:11914)

-21: GTCATCCTTGCATTTGCAGGCGCCGTCCTGAGCCGGC-------------GCCTG
ACGGCGAGAGCGACGACTTGGCAAGTCCGGGCGCA (SEQ ID NO:11919)

-890: TCATCCTTGCATTTTGCAGGCGCC---//----TTCCTAGGGGGAAATC (SEQ ID NO:11920)

FIG. 6A

Plant Ta137-1

SBEIIa-A

```
WT:    GTCATCCTTGCTTGCATTGCAGGCGCCGTCCTGAGCCGCGGCCCTCTCCAGGAAGGTCCTGGTGCCTGACGG
       TGAGAGCGACGACTTGGCAAGTCCGGCGCA (SEQ ID NO:11908)

-4:    GTCATCCTTGCATTGCAGGCGCCGTCCTGAGCCGCGGCCCTCTCCAG----GGTCCTGGTGCCTGACGG
       TGAGAGCGACGACTTGGCAAGTCCGGCGCA (SEQ ID NO:11921)

-7:    GTCATCCTTGCATTGCAGGCGCCGTCCTGAGCCGCGGCCCTCTCC-------GTCCTGGTGCCTGACGG
       TGAGAGCGACGACTTGGCAAGTCCGGCGCA (SEQ ID NO:11922)

-13:   GTCATCCTTGCATTGCAGGCGCCGTCCTGAGCCGCGGCCC-------------TCCTGGTGCCTGACGG
       TGAGAGCGACGACTTGGCAAGTCCGGCGCA (SEQ ID NO:11923)

-167:  TTTTCTCACTCTTTCTTCTGTGTTCTTGCTGTAACTGCAAGTT--//--GTACACACCATCGTGCCGGGAA
       ATCTTCATACAATCG (SEQ ID NO:11924)
```

SBEIIa-B

```
WT:    CTCATCCTTGCATTGCAGGCGCCGTCCTGAGCCGCGGCCCTCTCCAGGAAGGTCCTGGTGCCTGAC
       GGTGAGAGCGACGACTTGGCGGCCACTCCAGCGCA (SEQ ID NO:11911)

-17:   CTCATCCTTGCATTGCAGGCGCCGTCCTGAGCCG-------------AGGTCCTGGTGCCTGAC
       GGTGAGAGCGACGACTTGGCGGCCACTCCAGCGCA (SEQ ID NO:11925)
```

Plant Ta137-1
SBEIIa-D

WT:   GTCATCCTTGCATTTTGCAGGCGCCGTCCTGAGCCGCGGCGCCTCTCCAGGGAAGGTCCTGGTGCCTGA
      CGGCGAGAGCGACGACTTGGCAAGTCCGGGCGCA (SEQ ID NO:11914)

-6:   GTCATCCTTGCATTTTGCAGGCGCCGTCCTGAGCCGCGGCGCCTCTCCAG------TCCTGGTGCCTGA
      CGGCGAGAGCGACGACTTGGCAAGTCCGGGCGCA (SEQ ID NO:11926)

-10:  GTCATCCTTGCATTTTGCAGGCGCCGTCCTGAGCCGCGGCGCCTCTC----------GTCCTGGTGCCTGA
      CGGCGAGAGCGACGACTTGGCAAGTCCGGGCGCA (SEQ ID NO:11927)

-13:  GTCATCCTTGCATTTTGCAGGCGCCGTCCTGAGCCGCGGCGCCTCC-------------GTGCCTGA
      CGGCGAGAGCGACGACTTGGCAAGTCCGGGCGCA (SEQ ID NO:11928)

-14:  GTCATCCTTGCATTTTGCAGGCGCCGTCCTGAGCCGCGGCGCCT--------------CTGGTGCCTGA
      CGGCGAGAGCGACGACTTGGCAAGTCCGGGCGCA (SEQ ID NO:11929)

-15:  GTCATCCTTGCATTTTGCAGGCGCCGTCCTGAGCCGCGC---------------GGTCCTGGTGCCTGA
      CGGCGAGAGCGACGACTTGGCAAGTCCGGGCGCA (SEQ ID NO:11930)

Plant Ta139-1
SBEIIa-A
WT: GTCATCCTTGCATTGCAGGCGCCGTCCTGAGCCGGCGGCT CTCCAGGAAGGTCCTGGTGCCTGACGG
TGAGAGCGACGACTTGGCAAGTCCGGCGCA (SEQ ID NO:11908)

-4: GTCATCCTTGCATTGCAGGCGCCGTCCTGAGCCGGCGGCTCTC----AAGGTCCTGGTGCCTGACGG
TGAGAGCGACGACTTGGCAAGTCCGGCGCA (SEQ ID NO:11931)

SBEIIa-B
WT: CTCATCCTTGCATTGCAGGCGCCGTCCTGAGCCGGCGGCCTCTCCAGGAAGGTCCTGGTGCCTGAC
GGTGAGAGCGACGACTTGGCGGCCACTCCAGCGCA (SEQ ID NO:11911)

-4: CTCATCCTTGCATTGCAGGCGCCGTCCTGAGCCGGCCTCTCCAGG----TCCTGGTGCCTGAC
GGTGAGAGCGACGACTTGGCGGCCACTCCAGCGCA (SEQ ID NO:11932)

-10: CTCATCCTTGCATTGCAGGCGCCGTCCTGAGCCGGCGGCCTC----------CCTGGTGCCTGAC
GGTGAGAGCGACGACTTGGCGGCCACTCCAGCGCA (SEQ ID NO:11933)

-22: CTCATCCTTGCATTGCAGGCGCCGTCCTGAGCCGGCGGCCTCT---------------------AC
GGTGAGAGCGACGACTTGGCGGCCACTCCAGCGCA (SEQ ID NO:11934)

SBEIIa-D
WT: GTCATCCTTGCATTTGCAGGCGCCGTCCTGAGCCGGCGGCCT CTCCAGGAAGGTCCTGGTGCCTGA
CGGCGAGAGCGACGACTTGGCAAGTCCGGGCGCA (SEQ ID NO:11914)

-11: GTCATCCTTGCATTTGCAGGCGCCGTCCTGAGCCGGCGCCTCTCC--------TGGTGCCTGA
CGGCGAGAGCGACGACTTGGCAAGTCCGGGCGCA (SEQ ID NO:11935)

-17: GTCATCCTTGCATTTGCAGGCGCCGTCCTGAGCCGGCGGC----------------TGGTGCCTGA
CGGCGAGAGCGACGACTTGGCAAGTCCGGGCGCA (SEQ ID NO:11936)

FIG. 8

Plant Ta125-2-14

SBEIIa-A

-23: GTCATCCTTGCATTGCAGGCGCCGTCCTGAGCCGCGGCCT------------------G
ACGGTGAGAGCGACGACTTGGCAAGTCCGGCGCA (SEQ ID NO:11910)

-23: GTCATCCTTGCATTGCAGGCGCCGTCCTGAGCCGCGGCCT------------------G
ACGGTGAGAGCGACGACTTGGCAAGTCCGGCGCA (SEQ ID NO:11910)

SBEIIa-B

-4: CTCATCCTTGCATTTGCAGGCGCCGTCCTGAGCCGCGGCCTCTCCA----AGGTCCTGGTGCCTGAC
GGTGAGAGCGACGACTTGGCGGCCACTCCAGCGCA (SEQ ID NO:11912)

-4: CTCATCCTTGCATTTGCAGGCGCCGTCCTGAGCCGCGGCCTCTCCA----AGGTCCTGGTGCCTGAC
GGTGAGAGCGACGACTTGGCGGCCACTCCAGCGCA (SEQ ID NO:11912)

SBEIIa-D

-12: GTCATCCTTGCATTTGCAGGCGCCGTCCTGAGCCGCGGCC----------GTCCTGGTGCCTG
ACGGCGAGAGCGACGACTTGGCAAGTCCGGCGCA (SEQ ID NO:11916)

-12: GTCATCCTTGCATTTGCAGGCGCCGTCCTGAGCCGCGGCC----------GTCCTGGTGCCTG
ACGGCGAGAGCGACGACTTGGCAAGTCCGGCGCA (SEQ ID NO:11916)

FIG. 9

Plant Ta125-2-44-1-1a (-23/-23, -4/-4, -4/-4)

SBEIIa-A

-23: GTCATCCTTGCATTGCAGGCGCCGTCCTGAGCCGCGGCCT----------------G
ACGGTGAGAGCGACGAGCTTGGCAAGTCCGGCGCA (SEQ ID NO:11910)

-23: GTCATCCTTGCATTGCAGGCGCCGTCCTGAGCCGCGGCCT----------------G
ACGGTGAGAGCGACGAGCTTGGCAAGTCCGGCGCA (SEQ ID NO:11910)

SBEIIa-B

-4: CTCATCCTTGCATTTGCAGGCGCCGTCCTGAGCCGGCCTCTCCA----AGGTCCTGGTGCCTGAC
GGTGAGAGCGACGACTTGGCGGCCACTCCAGCGCA (SEQ ID NO:11912)

-4: CTCATCCTTGCATTTGCAGGCGCCGTCCTGAGCCGGCCTCTCCA----AGGTCCTGGTGCCTGAC
GGTGAGAGCGACGACTTGGCGGCCACTCCAGCGCA (SEQ ID NO:11912)

SBEIIa-D

-4: GTCATCCTTGCATTTGCAGGCGCCGTCCTGAGCCGGCCTCTCCA----AGGTCCTGGTGCCTGA
CGGCGAGAGCGACGACTTGGCAAGTCCGGCGCA (SEQ ID NO:11915)

-4: GTCATCCTTGCATTTGCAGGCGCCGTCCTGAGCCGGCCTCTCCA----AGGTCCTGGTGCCTGA
CGGCGAGAGCGACGACTTGGCAAGTCCGGCGCA (SEQ ID NO:11915)

FIG. 10

Plant Ta125-2-44-1-2a (-23/-23, -20/-20, -4/-4)

SBEIIa-A

-23: GTCATCCTTGCATTGCAGGCGCCGTCCTGAGCCGCGCGGGCCT---------------------------GA
CGGTGAGAGCGACGACTTGGCAAGTCCGGCGCA (SEQ ID NO:11910)

-23: GTCATCCTTGCATTGCAGGCGCCGTCCTGAGCCGCGCGGGCCT---------------------------GA
CGGTGAGAGCGACGACTTGGCAAGTCCGGCGCA (SEQ ID NO:11910)

SBEIIa-B

-20: CTCATCCTTGCATTTGCAGGCGCGTCCTGAGCCGCGGC----------------------TGCCTGAC
GGTGAGAGCGACGACTTGGCGGCCACTCCAGCGCA (SEQ ID NO:11913)

-20: CTCATCCTTGCATTTGCAGGCGCGTCCTGAGCCGCGGC----------------------TGCCTGAC
GGTGAGAGCGACGACTTGGCGGCCACTCCAGCGCA (SEQ ID NO:11913)

SBEIIa-D

-4: GTCATCCTTGCATTTTGCAGGCGCCGTCCTGAGCCGCGGCCTCTCCA----AGGTCCTGGTGCCTGAC
GGCGAGAGCGACGACTTGGCAAGTCCGGCGCA (SEQ ID NO:11915)

-4: GTCATCCTTGCATTTTGCAGGCGCCGTCCTGAGCCGCGGCCTCTCCA----AGGTCCTGGTGCCTGAC
GGCGAGAGCGACGACTTGGCAAGTCCGGCGCA (SEQ ID NO:11915)

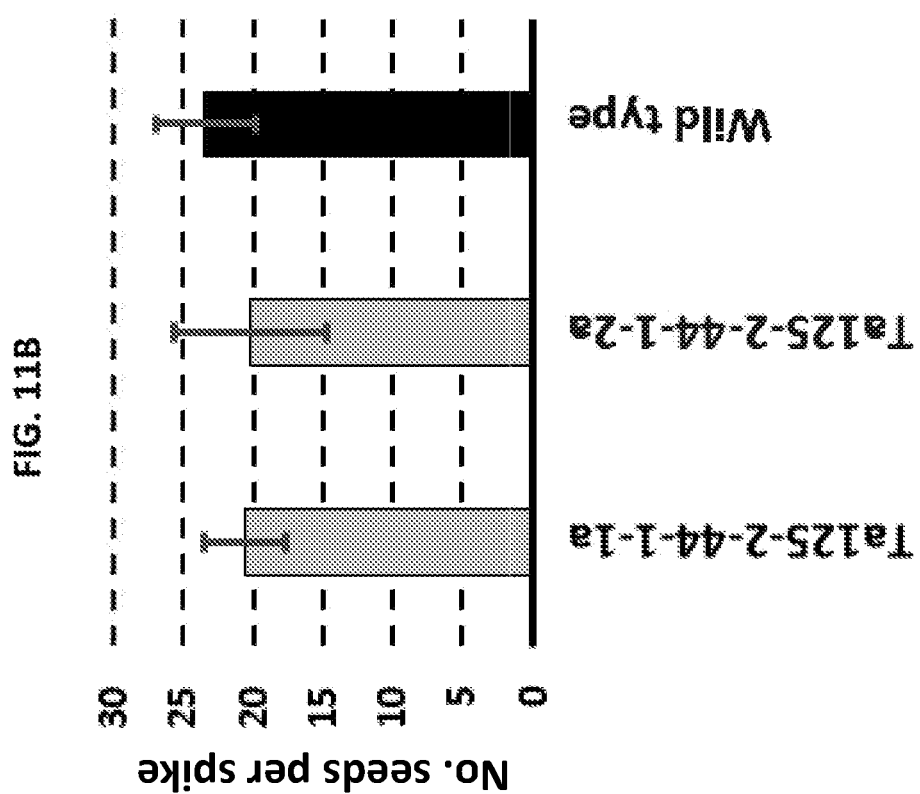

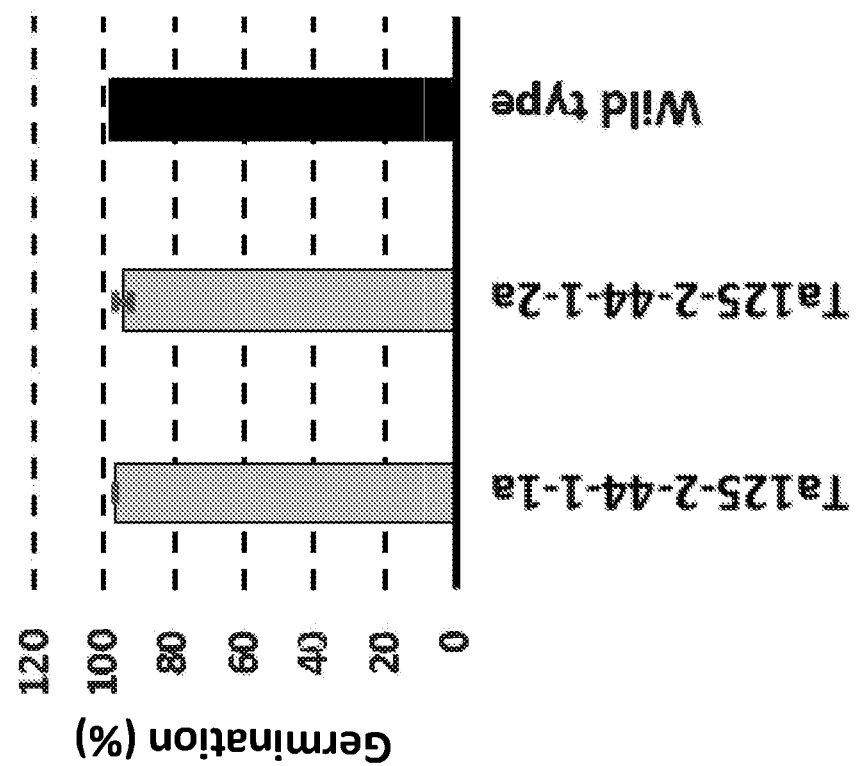

ENGINEERING WHEAT WITH INCREASED DIETARY FIBER

CROSS-REFERENCE TO RELATED APPLICATIONS

This application claims benefit of priority from U.S. Provisional Application Ser. No. 62/665,643, filed May 2, 2018.

SEQUENCE LISTING

The instant application contains a Sequence Listing which has been submitted electronically via EFS-Web in ASCII format. The ASCII copy, created on May 6, 2022, is named C1633148101_SequenceListing_substitute.txt and is 8,836 kb in size.

TECHNICAL FIELD

This document provides materials and methods for generating wheat varieties with increased amylose content.

BACKGROUND

Wheat (*Triticum aestivum*) is one of the most-produced crops worldwide, with an estimated annual production of 713 million tons (Food and Agricultural Organization of the United Nations, 2010 Crop Production Data, online at faostat.fao.org/site/567/DesktopDefault.aspx?PageID=567#ancor). Wheat grain is used to make flour for breads, cakes, pastas, and biscuits, and to make beer. One of the major nutritional components in wheat flour is starch. Wheat starch consists of glucose monomers connected by α1,4 and α1,6 linkages. The resulting polymers are grouped into two classes: amylose and amylopectin. Amylopectin has mostly α1,6 linkages and is highly branched, while amylose has mostly α1,4 linkages and is largely unbranched. Due to their relatively linear structure, amylose molecules are tightly packed and are insoluble, and are more resistant to digestion than amylopectin (Tetlow, *Seed Science Research*, 21:5-32, 2011).

SUMMARY

This document provides materials and methods for generating wheat varieties with increased levels of amylose, resistant starch, and dietary fiber, relative to the levels in corresponding wild type wheat varieties. Starch within wheat grains typically is comprised of about 25% amylose and 75% amylopectin. Due to its highly branched structure, amylopectin is quickly degraded, making it a rich source for glucose. On the other hand, amylose has a tightly packed structure and is more resistant to digestion. Foods high in resistant starches have the potential to lower the rate of glucose entry into circulation, and to decrease the risk of diet-related noninfectious chronic diseases, including heart disease, colon cancer, and diabetes (see, e.g., Regina et al., *Proc Natl Acad Sci USA*, 103:3546-3551, 2006; Kendall et al., *J AOAC Int*, 87:769-774, 2004; Brouns et al., *Trends Food Sci Tech*, 13:251-261, 2002; and Bird et al., *Beneficial Microbes*, 1:423-431, 2010).

Branch formation in amylopectin is catalyzed by starch-branching enzymes that cleave internal α1,4 bonds and transfer the reducing ends to C-6 hydroxyls. In wheat, branch formation is regulated by two classes of starch-branching enzymes (SBEs), SBEI and SBEII. This disclosure is based, at least in part, on the discovery that wheat varieties with increased levels of amylose, resistant starch, and dietary fiber can be generated using sequence-specific nucleases to make targeted mutations or knockouts of the SBEII genes and their alleles. The modified wheat varieties can have enhanced nutritional qualities as compared to non-modified wheat varieties. Further, the modified wheat varieties do not carry foreign DNA and therefore may have reduced regulatory burden. This document also is based, at least in part, on the development of wheat varieties with loss-of-function SBEII mutations that are created by sequence-specific nucleases. Thus, in some embodiments, this document provides a *Triticum* plant, plant part, or plant cell having a mutation in at least two SBEII alleles from the SBEIIa and/or SBEIIb genes (e.g., at least two SBEII alleles, at least four SBEII alleles, at least six SBEII alleles, at least at least eight SBEII alleles, or at least twelve SBEII alleles) endogenous to the plant, plant part, or plant cell such that the plant, plant part, or plant cell has reduced expression of SBEII alleles as compared to a control *Triticum* plant, plant part, or plant cell that lacks the mutation.

In a first aspect, this document features a *Triticum* plant, plant part, or plant cell comprising a deletion or insertion in at least two SBEII alleles endogenous to the plant, plant part, or plant cell, wherein the deletion or insertion was made using a rare-cutting endonuclease. The at least two SBEII alleles can include SBEIIa alleles, SBEIIb alleles, or SBEIIa and SBEIIb alleles. The at least two SBEII alleles each can have a deletion of one or more nucleotide base pairs. The at least two SBEII alleles each can include an insertion of one or more nucleotide base pairs endogenous to the plant, plant part, or plant cell. The plant, plant part, or plant cell can have a deletion of one or more SBEII alleles. The insertion or deletion can be at a target sequence as set forth in SEQ ID NO:1, or at a target sequence having at least 90% identity to SEQ ID NO:1. The rare-cutting endonuclease can be a transcription activator-like effector endonuclease (TALE nuclease). The TALE nuclease can bind to a sequence as set forth in SEQ ID NO:1. In some cases, the SBEII alleles can be SBEIIa alleles, where every endogenous SBEIIa allele has a deletion or insertion. The at least two SBEII alleles can be SBEIIa alleles, where the SBEIIa alleles include the sequences set forth in SEQ ID NO:11910, 11912, and 11915, or the sequences set forth in SEQ ID NO:11910, 11913, and 11915. The at least two SBEII alleles can be SBEIIb alleles, where every endogenous SBEIIb allele has a deletion or insertion. In some cases, every endogenous SBEIIa and SBEIIb allele can have a deletion or insertion. Each of the at least two SBEII alleles can exhibit removal of an endogenous nucleic acid, without including any exogenous nucleic acid. The plant part can be grain. The grain can be milled, ground, pearled, rolled, kibbled, par-boiled, or cracked grain. The *Triticum* plant, plant part, or plant cell can be of the species *Triticum aestivum, Triticum aethiopicum, Triticum araraticum, Triticum boeoticum, Triticum carthhcum, Triticum compactum, Triticum dicoccoides, Triticum dicoccon, Triticum durum, Triticum ispahanicum, Triticum karamyschevii, Triticum macha, Triticum militinae, Triticum monococcum, Triticum polonicum, Triticum spelta, Triticum sphaerococcum, Triticum timopheevii, Triticum turanicum, Triticum turgidum, Triticum urartu, Triticum vavilovii,* or *Triticum zhukovskyi*. The plant, plant part, or plant cell can have increased levels of dietary fiber as compared to a control plant, plant part, or plant cell that lacks the deletion or insertion.

In another aspect, this document features a method for generating a *Triticum* plant that has increased levels of dietary fiber, where the method includes (a) contacting a *Triticum* plant cell or plant part having functional SBEII alleles with a rare-cutting endonuclease targeted to an endogenous SBEII allele, (b) selecting from the plant cell or plant part a plant cell or plant part in which at least one SBEII allele has a deletion or insertion due, at least in part, to nuclease activity of the rare-cutting endonuclease, and (c) growing the selected plant cell or plant part into a *Triticum* plant, where the *Triticum* plant has increased levels of dietary fiber as compared to a control *Triticum* plant in which the SBEII alleles have not been mutated. The rare-cutting endonuclease can be a TALE nuclease, Cas9/gRNA, zinc-finger nuclease, or meganuclease. The *Triticum* plant cell can be s a protoplast. The contacting can include transforming the protoplast with a nucleic acid encoding the rare-cutting endonuclease. The nucleic acid can be an mRNA, or can be contained within a vector. The method can further include culturing the protoplast to generate a plant line. The method can further include isolating genomic DNA comprising at least a portion of the at least one SBEII allele from the protoplast. The *Triticum* plant part can be an immature embryo, embryogenic callus, or scutella. The contacting can include transforming the immature embryo, embryogenic callus, or scutella with a nucleic acid encoding the rare-cutting endonuclease. The transforming can include *Agrobacterium*-mediated transformation or biolistics. The method can further include culturing the immature embryo, embryogenic callus, or scutella to generate a plant line. The method can further include isolating genomic DNA comprising at least a portion of the at least one SBEII allele from the immature embryo, embryogenic callus, or scutella. The deletion or insertion can be at a target sequence as set forth in SEQ ID NO:1, or at a target sequence having at least 90% identity to SEQ ID NO:1. The selected plant cell or plant part can have a deletion or insertion in two or more endogenous SBEIIa alleles. The two or more SBEIIa alleles can contain the sequences set forth in SEQ ID NO:11910, 11912 and 11915, or the deletions shown in SEQ ID NO:11910, 11913, and 11915. The *Triticum* plant cell or plant part can be of the species *Triticum aestivum, Triticum aethiopicum, Triticum araraticum, Triticum boeoticum, Triticum carthhcum, Triticum compactum, Triticum dicoccoides, Triticum dicoccon, Triticum durum, Triticum ispahanicum, Triticum karamyschevii, Triticum macha, Triticum militinae, Triticum monococcum, Triticum polonicum, Triticum spelta, Triticum sphaerococcum, Triticum timopheevii, Triticum turanicum, Triticum turgidum, Triticum urartu, Triticum vavilovii,* or *Triticum zhukovskyi*.

In another aspect, this document features a *Triticum* plant, plant part, or plant cell having a mutation in at least two SBEII alleles endogenous to the plant, plant part, or plant cell, such that the plant, plant part, or plant cell has reduced expression of SBEII as compared to a control *Triticum* plant, plant part, or plant cell that lacks the mutation. The at least two SBEII alleles can be SBEIIa alleles, SBEIIb alleles, or SBEIIa and SBEIIb alleles. Each mutation can be a deletion of one or more nucleotide base pairs, or an insertion of one or more nucleotide base pairs endogenous to the plant, plant part, or plant cell. The mutation can include a deletion of one or more SBEII alleles. In some embodiments, the mutation can include a combination of two or more of: deletion of one or more alleles, inversion of one or more alleles, insertion of one or more nucleotides within an allele, deletion of one or more nucleotides from an allele, and substitution of one or more nucleotides within an allele. The mutation can be at a target sequence as set forth in SEQ ID NO:1, or at a target sequence having at least 90% identity to SEQ ID NO:1. The plant, plant part, or plant cell can be made using a rare-cutting endonuclease (e.g., a TALE nuclease). The TALE nuclease can bind to a sequence as set forth in SEQ ID NO:1. Every endogenous SBEIIa allele can be mutated, and in some cases, the plant, plant part, or plant cell may have no detectable expression of SBEIIa. Every endogenous SBEIIb allele can be mutated, and in some cases, the plant, plant part, or plant cell may have no detectable expression of SBEIIb. In some embodiments, every endogenous SBEIIa and SBEIIb allele can be mutated, and in some cases, the plant, plant part, or plant cell may have no detectable expression of SBEIIa and SBEIIb. Each of the at least two SBEII alleles can exhibit removal of an endogenous nucleic acid, without including any exogenous nucleic acid. The *Triticum* plant, plant part, or plant cell can be of the species *Triticum aestivum, Triticum aethiopicum, Triticum araraticum, Triticum boeoticum, Triticum carthlicum, Triticum compactum, Triticum dicoccoides, Triticum dicoccon, Triticum durum, Triticum ispahanicum, Triticum karamyschevii, Triticum macha, Triticum militinae, Triticum monococcum, Triticum polonicum, Triticum spelta, Triticum sphaerococcum, Triticum timopheevii, Triticum turanicum, Triticum turgidum, Triticum urartu, Triticum vavilovii,* or *Triticum zhukovskyi*. The plant, plant part, or plant cell can have increased levels of amylose as compared to a control plant, plant part, or plant cell that lacks the mutation.

In another aspect, this document features a method for generating a *Triticum* plant that has increased levels of amylose. The method can include (a) contacting a *Triticum* plant cell or plant part having functional SBEII alleles with a rare-cutting endonuclease targeted to an endogenous SBEII allele; (b) selecting from the plant cell or plant part a plant cell or plant part in which at least one SBEII allele has a mutation due, at least in part, to nuclease activity of the rare-cutting endonuclease; and (c) growing the selected plant cell or plant part into a *Triticum* plant, wherein the *Triticum* plant has increased levels of amylose as compared to a control *Triticum* plant in which the SBEII alleles have not been mutated. The rare-cutting endonuclease can be a TALE nuclease, Cas9/gRNA, zinc-finger nuclease, or meganuclease. The *Triticum* plant cell can be a protoplast. The contacting can include transforming the protoplast with a nucleic acid encoding the rare-cutting endonuclease. The nucleic acid can be an mRNA. The nucleic acid can be contained within a vector. The method can further include culturing the protoplast to generate a plant line, and/or isolating genomic DNA containing at least a portion of the at least one SBEII allele from the protoplast. The *Triticum* plant part can be an immature embryo, embryogenic callus, or scutella. The contacting can include transforming the embryo, embryogenic callus, or scutella with a nucleic acid encoding the rare-cutting endonuclease. The transforming can include *Agrobacterium*-mediated transformation or biolistics. The method can further include culturing the immature embryo, embryogenic callus, or scutella to generate a plant line, and/or isolating genomic DNA containing at least a portion of the at least one SBEII allele from the immature embryo, embryogenic callus, or scutella. The mutation can be at a target sequence as set forth in SEQ ID NO:1, or at a target sequence having at least 90% identity to SEQ ID NO:1. The selected plant cell or plant part can have a mutation in two or more endogenous SBEII alleles. The *Triticum* plant cell or plant part can be of the species *Triticum aestivum, Triticum aethiopicum, Triticum araraticum, Triticum boeoticum, Triticum carthhcum, Triticum compactum, Triticum dicoccoides, Triticum dicoccon, Triticum durum, Triticum ispahanicum, Triticum karamyschevii,*

*Triticum macha, Triticum militinae, Triticum monococcum, Triticum polonicum, Triticum spelta, Triticum sphaerococcum, Triticum timopheevii, Triticum turanicum, Triticum turgidum, Triticum urartu, Triticum vavilovii,* or *Triticum zhukovskyi.*

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows the *T. aestivum* nucleotide sequences of exon 2 from SBEIIa-A (SEQ ID NO:11890), exon 3 from SBEIIa-A (SEQ ID NO:11891), exon 2 from SBEIIa-B (SEQ ID NO:11892), exon 3 from SBEIIa-B (SEQ ID NO:11893), exon 2 from SBEIIa-D (SEQ ID NO:11894), and exon 3 from SBEIIa-D (SEQ ID NO:11895).

FIG. 3 shows target sequences for TALE nuclease pairs SBEIIa_T1, SBEIIa_T2, and SBEIIa_T3. Specifically, target sequences are shown for SBEIIa_T1 in the SBEIIa-A gene (SEQ ID NO:11896), SBEIIa-B gene (SEQ ID NO:11896), and SBEIIa-D gene (SEQ ID NO:11897); for SBEIIa_T2 in the SBEIIa-A gene (SEQ ID NO:11898), SBEIIa-B gene (SEQ ID NO:11899), and SBEIIa-D gene (SEQ ID NO:11899); and for SBEIIa_T3 in the SBEIIa-A gene (SEQ ID NO:11900), SBEIIa-B gene (SEQ ID NO:11900), and SBEIIa-D gene (SEQ ID NO:11901).

FIG. 4 shows the mutations in the SBEIIa-A, B and D genes from plant Ta125-2. The SBEIIa-A gene had a 2 bp insertion (SEQ ID NO:11909) and a 23 bp deletion (SEQ ID NO:11910). The SBEIIa-B gene had a 4 bp deletion (SEQ ID NO:11912) and a 20 bp deletion (SEQ ID NO:11913). The SBEIIa-D gene had a 4 bp deletion (SEQ ID NO:11915) and a 12 bp deletion (SEQ ID NO:11916).

FIG. 5 shows the mutations in the SBEIIa-B and D genes from plant Ta128-1. The SBEIIa-B gene had a 1 bp insertion (SEQ ID NO:11917) and a 1 bp deletion (SEQ ID NO:11918). The SBEIIa-D gene had a 21 bp deletion (SEQ ID NO:11919) and an 890 bp deletion (SEQ ID NO:11920).

FIGS. 6A and 6B show the mutations in the SBEIIa-A, B and D genes from plant Ta137-1. The SBEIIa-A gene had a 4 bp deletion (SEQ ID NO:11921), a 7 bp deletion (SEQ ID NO:11922), a 13 bp deletion (SEQ ID NO:11923), and a 167 bp deletion (SEQ ID NO:11924). The SBEIIa-B gene had a 17 bp deletion (SEQ ID NO:11925). The SBEIIa-D gene had a 6 bp deletion (SEQ ID NO:11926), 10 bp deletion (SEQ ID NO:11927), 13 bp deletion (SEQ ID NO:11928), 14 bp deletion (SEQ ID NO:11929) and 15 bp deletion (SEQ ID NO:11930).

FIG. 7 shows the mutations in the SBEIIa-A, B and D genes from plant Ta139-1. The SBEIIa-A gene had a 4 bp deletion (SEQ ID NO:11931). The SBEIIa-B gene had a 4 bp deletion (SEQ ID NO:11932), 10 bp deletion (SEQ ID NO:11933), and 22 bp deletion (SEQ ID NO:11934). The SBEIIa-D gene had a 11 bp deletion (SEQ ID NO:11935) and a 17 bp deletion (SEQ ID NO:11936).

FIG. 8 shows the mutations in the SBEIIa-A, B and D genes from plant Ta125-2-14. Both SBEIIa-A alleles had a 23 bp deletion (SEQ ID NO:11910). Both SBEIIa-B alleles had a 4 bp deletion (SEQ ID NO:11912). Both SBEIIa-D alleles had a 12 bp deletion (SEQ ID NO:11916).

FIG. 9 shows the mutations in the SBEIIa-A, B and D genes from plant Ta125-2-44-1-1a (-23/-23, -4/-4, -4/-4). Both SBEIIa-A alleles had a 23 bp deletion (SEQ ID NO:11910). Both SBEIIa-B alleles had a 4 bp deletion (SEQ ID NO:11912). Both SBEIIa-D alleles had a 4 bp deletion (SEQ ID NO:11915).

FIG. 10 shows the mutations in the SBEIIa-A, B and D genes from plant Ta125-2-44-1-2a (-23/-23, -20/-20, -4/-4). Both SBEIIa-A alleles had a 23 bp deletion (SEQ ID NO:11910). Both SBEIIa-B alleles had a 20 bp deletion (SEQ ID NO:11913). Both SBEIIa-D alleles had a 4 bp deletion (SEQ ID NO:11915).

FIGS. 11A-11C are graphs plotting plant height (FIG. 11A), number of seeds per spike (FIG. 11B), and germination efficiency (FIG. 11C) for *T. aestivum* plants with complete knockout mutations within SBEIIa alleles (Ta125-2-44-1-1a and Ta125-2-44-1-2a) as compared to wild type.

DETAILED DESCRIPTION

Figure 2:
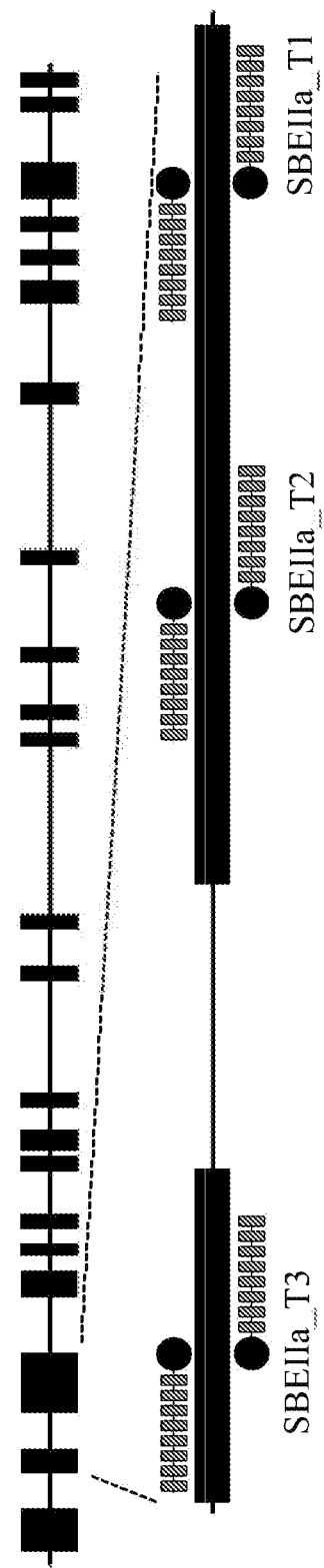
FIG. 2 is an illustration of an SBEIIa gene and the relative TALE nuclease binding sites for TALE nuclease pairs SBEIIa_T1, SBEIIa_T2, and SBEIIa_T3.

This document provides materials and methods for generating wheat varieties with increased levels of amylose, resistant starch, and dietary fiber relative to corresponding wild type wheat varieties. Wheat starches typically are composed of about 25% amylose (linear chains of glucose connected by α1,4 linkages) and 75% amylopectin (linear chains of glucose with frequent branching by α1,6 linkages). Amylopectin is quickly degraded due to its highly branched structure, which provides many sites to which enzymes can bind. Amylopectin therefore is a rich source for glucose. Branch formation within amylopectin is catalyzed by starch-branching enzymes, which cleave internal α1,4 bonds and transfer the reducing ends to C-6 hydroxyls. In wheat, branch formation is regulated by two classes of starch-branching enzymes (SBEs): SBEI and SBEII. The SBEII class is most responsible for amylopectin synthesis, as loss of SBEI has minimal effects on starch synthesis and composition (Blauth et al., *Plant Mol Biol,* 48:287-297, 2002). The SBEII class includes two gene products, SBEIIa and SBEIIb, which have distinct tissue-specific expression patterns. While SBEIIb is expressed exclusively in nonphotosynthetic storage tissues (endosperm), SBEIIa is ubiquitously expressed, and is expressed at much higher levels than SBEIIb within wheat endosperm (Blauth et al., Planta, 222:899-906, 2005).

The ratio of amylose to amylopectin in wheat can be altered by modifying the expression profile of enzymes involved in starch synthesis. For example, SBEIIa knockdown can be achieved using RNAi technology (Regina et al., *Proc Natl Acad Sci USA,* 103:3546-3551, 2006; and Sestili et al., *BMC Plant Biology,* 10:144, 2010) or by TILLING (Targeting Induced Local Lesions in Genomes; Slade et al., *BMC Plant Biology,* 12:69, 2012; Hazard et al., *Crop Science,* 52:1754-1766, 2012). Using such techniques, wheat varieties have been generated containing ratios of amylose to amylopectin ranging from ~40:60 to 70:30, as compared to the ~25:75 ratio in wild type plants. These technologies frequently result in incomplete silencing or inactivation of the target gene, such that residual enzyme activity may prevent the maximum possible phenotypic change. RNAi also requires the creation of transgenic lines that stably express the RNA sequence over multiple generations.

As described herein, by using sequence-specific nucleases, a maximum level of amylose content can be achieved through complete gene knockout. Efforts to engineer high amylose in wheat using sequence-specific nucleases must address challenges related to the complexity of the wheat genome. For example, the bread wheat genome is allohexaploid, with three different genomes (termed A, B, and D), and is 17 Gbp in size—five times larger than the human genome. In addition, a high percentage (80-90%) of the genome is repetitive sequence. Efforts are further challenged by the three non-identical homoeoalleles of SBEIIa and SBEIIb.

This document provides strategies for using sequence-specific nucleases to successfully target the SBEII alleles within wheat. This document also provides wheat plant varieties (e.g., *T. aestivum* varieties) that contain increased levels of amylose, resistant starch, and dietary fiber. Methods for generating such plant varieties also are provided.

As used herein, the terms "plant" and "plant part" refer to cells, tissues, organs, grains, and severed parts (e.g., roots, leaves, and flowers) that retain the distinguishing characteristics of the parent plant. "Grain" refers to any plant structure that is formed by continued differentiation of the ovule of the plant, following its normal maturation point, irrespective of whether it is formed in the presence or absence of fertilization and irrespective of whether or not the grain structure is fertile or infertile.

The term "allele(s)" means any of one or more alternative forms of a gene at a particular locus. In a diploid (or amphidiploid) cell of an organism, alleles of a given gene are located at a specific location or locus on a chromosome, with one allele being present on each chromosome of the pair of homologous chromosomes. Similarly, in a hexaploid cell of an organism, one allele is present on each chromosome of the group of six homologous chromosomes. In a tetraploid cell, one allele is present on each chromosome of the group of four homologous chromosomes. "Heterozygous" alleles are different alleles residing at a specific locus, positioned individually on corresponding homologous chromosomes. "Homozygous" alleles are identical alleles residing at a specific locus, positioned individually on corresponding homologous chromosomes in the cell.

The term "gene" as used herein refers to a sequence of DNA that encodes a protein. "SBEII genes" are sequences of DNA endogenous to the wheat genome that encode SBEIIa or SBEIIb proteins. "SBEIIa genes" are sequences of DNA endogenous to the wheat genome that encode SBEIIa proteins. "SBEIIb genes" are sequences of DNA endogenous to the wheat genome that encode SBEIIb proteins. The term "SBEII genes" also refers to alleles of SBEII genes that are present at the same chromosomal position on homologous chromosomes. A "wild type SBEII gene" is a naturally occurring SBEII gene (e.g., as found within naturally occurring *T. aestivum* plants) that encodes an SBEIIa or SBEIIb protein, while a "mutant SBEII gene" is an SBEII gene that has incurred one or more sequence changes, where the sequence changes result in the loss or modification of amino acids within the translated protein, as compared to the wild type SBEII gene. Such a "mutant SBEII gene" can include one or more mutations in an SBEII gene's nucleic acid sequence, where the mutation(s) result in absence or reduced levels of SBEIIa or SBEIIb proteins in the plant or plant cell in vivo. Additionally, a "mutant SBEII gene" can include an SBEII gene for which the full length coding sequence has been deleted from the wheat genome, such that it is no longer capable of producing SBEII protein. Further, a "mutant SBEII gene" can include an SBEII gene in which an in-frame insertion or deletion has occurred in a region of the gene coding sequence that encodes essential amino acids for SBEIIa or SBEIIb protein function.

Many *Triticum* species are hexaploid and contain three different genomes, termed A, B, and D. Accordingly, there are three SBEIIa genes, one on each of the three genomes in such *Triticum* species, resulting in a total of six SBEIIa alleles in the wheat genome. The SBEIIa gene present on the A genome has two alleles and is referred to herein as SBEIIa-A; the SBEIIa gene present on the B genome has two alleles and is referred to herein as SBEIIa-B; and the SBEIIa gene present on the D genome has two alleles and is referred to herein as SBEIIa-D. The methods provided herein can be used to inactivate all six SBEIIa alleles using one or more TALE nuclease pairs. Other *Triticum* species are diploid or tetraploid. The methods provided herein can be used to inactivate both or all four SBEIIa alleles of such diploid or tetraploid species using one or more TALE nuclease pairs.

The term "high amylose" or "high levels of amylose" as used herein refers to differences in the ratio of amylose to amylopectin in modified wheat plants, as compared to non-modified wheat plants. Specifically, the ratio of amylose to amylopectin in modified plants is increased compared to non-modified plants (e.g., if most wild type wheat plants contain a ratio of 25:75, then the ratio in a modified plant can be 30:70, 40:60, 50:50, 60:40, 70:30, 80:20, 90:10, or 100:0). "High amylose" also refers to modified wheat plants having decreased levels of amylopectin.

A representative example of a naturally occurring *T. aestivum* SBEIIa nucleotide sequence from the A genome is shown in SEQ ID NO:1:

```
                                                     (SEQ ID NO: 1)
ATGGCGACGTTTGCGGTGTCCGGCGCGACCCTCGGTGTGGCGCGGCCCGCCGGCGCCGGCGG

CGGACTGCTGCCGCGATCCGGCTCGGAGCGGAGGGGCGGGGTGGACCTGCCGTCGCTGCTCC

TCAGGAAGAAGGACTCCTCTCGTACGCCTCGCTCGCTCGCTCCAATCTCCCCGTCCATTTTT

GCCCCCCTTCTCTCTCCCTATCTGCGCGCGCATGGCCTGTTCGATGCTGTTCCCCAGTTGAT

CTCCATCAACGAGAGAGATAGCTGGATTAGGCGATCGCCTGCGTCAGTGTCACCCAGGCCCT

GGTGTTATCACGGCTTTGATCATCTCCTCCCATTCTGATATTTTCTCACTCTTTCTTCTGTT
```

-continued

CTTGCTGTAACTGCAAGTTGTAGCATTGTCTCACTATTGTAGTCATCCTTGCATTGCAGGCG

CCGTCCTGAGCCGCGCGGCCTCTCCAGGGAAGGTCCTGGTGCCTGACGGTGAGAGCGACGAC

TTGGCAAGTCCGGCGCAACCTGAAGAATTACAGGTACACACCATCGTGCCGGGAAATCTTCA

TACAATCGTTATTCACTTACCAAATGCCGGATGAAACCAAGCCGCGGAGGCGTCAGGTTTTG

AGCTTCTTCTATCAGCATTGTGCAGTACTGCACTGCCTTGTGCATTTTGTTAGCCGTGGCCC

CGTGCTGGCTCTTGGGCCACTGAAAACTCAGATGGATGTGCATTCTAGCAAGAACTTCACGA

AATAATGCACTGTTTGTGGTTTCGTTAGTCTGCTCTACAATTGCTATTTTCGTGCTGTAGAT

ACCTGAAGACATCGAGGAGCAAACGGCTGAAGTAAACATGACAGGGGGGACTGCAGAAAAAC

TTGAATCTTCAGAACCGACTCAAGGCATTGTGGAAACAATCACTGATGGTGTAACCAAGGA

GTTAAGGAACTAGTCGTGGGGGAGAAACCGCGAGTTGTCCCAAAACCAGGAGATGGGCAGAA

AATATACGAGATTGACCCAACGCTGAAAGATTTTCGGAGCCATCTTGACTACCGGTAATGCC

TACCCGCTACTTTCGCTCATTTTGAATTAAGGTCCTTTCGTCATGCAAATTTGGGGAACATC

AAAGAGACAAAGACTAGGGACCACTATTTCTTACAGTTCCCCTCATGGTCTGAGAATATGCT

GGGACGTAGATGTATAATTGATGGCTACAATTTGCTCATAATTACGATACAAATAACTGTCT

CTGATCATTGCAATTACAGAGTGGCAAACTGATTAAAATGTGATAGATGGGTTATAGATTTT

ACTTTGCTAATTCCTCTACCAAATTCCTGGGGAAAAAAATCTACCAGTTGGGCAACTTAGTT

TCTTATCTTTGTTGCCTCTTTGTTTGGGGAAAACACACTGCTAAATTTGAATGATTTTGGG

TATGCCTCCGTGGATTCAACAGATACAGCGAATACAGGAGAATTCGTGCTGCTATTGACCAA

CATGAAGGTGGATTGGAAGCATTTTCTCGTGGTTATGAAAAGCTTGGATTTACCCGCAGGTA

AATTTAAAGCTTCAGTATTATGAAGCGCCTCCACTAGTCTACTTGCATATCTTACAAGAAAA

TTTATAATTCCTGTTTTCGCCTCTCTTTTTTCCAGTGCTGAAGGTATTGTCTAGTTGCATAT

CTTATAAGAAAATTTATGTTCCTGTTTTCCCCTATTTTCCAGTGCTGAAGGTATCACTTACC

GAGAATGGGCTCCTGGAGCGCATGTACGTCTTTTAAGTCTTAACAGACACCTTCCAATTCAT

TGTTAATGGTCACACTATTCACCAACTAGCTTACTGGACTTACAACTTAGCTTACTGAATAC

TGACCAGTTGCTCTAAATTTATGATCTGGCTTTTGCATCCTATTACAGTCTGCAGCATTAGT

AGGTGACTTCAACAATTGGAATCCGAATGCAGATACTATGACCAGAGTATGTCTACAGCTTG

GCAATCTTCCACCTTTGCTTCATAACTACTGATACATCTATTTGTATTTATTTTGCTGTTTG

CACATTCCTTAAAGTTGAGCCTCAACTATATCATATCAAAATGGTATAATTTGTCAGTGTCT

TAAGCTTCAGCCTAAAGATTCTACTGAAATTGGTCCATCTTTTTGAGATTGAAAATGAGTAT

ATTAAGGATGGATGAATAGGTGCAACACTCCCATTCTTTGGTAGAACCTTCTGCATTATGTG

TGTTTTTTCATCTACAATGAGCATATTTCCATGCTATCAGTGAAGGTTTGCTCCTATTGATG

CCGATATTTGATATGATCTTTTCAGGATGATTATGGTGTTTGGGAGATTTTCCTCCCTAACA

ATGCTGATGGATCCCCAGCTATTCCTCATGGCTCACGTGTAAAGGTAAGCTGGCCAATTATT

TAGTTGAGCATGTAGCATTTTCGAACTCTGCCCACTAAGGGTCCCTTTGCCTTTCTGTTTTC

TAGATACGGATGGATACTCCATCTGGTGTGAAGGATTCAATTTCTGCTTGGATCAAGTTCTC

TGTGCAGGCTCCAGGTGAAATACCATTCAATGGCATATATTATGATCCACCTGAAGAGGTAA

GTATCGATCTCCATTACATTATTAAATGAAATTTCCAGTGTTACGGTTTTTTAATACCCATT

TCGTGTCTCACTGACATGTGAGTCAAGACAATACTTTAGAATTTGGAAGTGACATATGCATT

AATTCACCTTCTAAGGGCTAAGGGGCAAGCAACCATGGTGATGTTTGTATGCTTGTGTGTGA

CTTAAGATCTTATAGCTCTTTTATGTGTTCTCTGTTGGTTAGGATATTCCATTTTGACCTTT

TGTGACCATTTACTAAGGATATTTTACATGCAAATGCAGGAGAAGTATGTCTTCCAACATCC

```
-continued
TCAACCTAAACGACCAGAGTCACTGAGGATTTATGAATCACACATTGGAATGAGCAGCCCAG

TATGTCAATAAGTTATTTCACCTGTTTCTGGTCTGATGGTCTATTCTATGGATTTTTTAGTT

CTGTTATGTATTGTTAACATATAACATGGTGCATTCACGTGACAACCTCGATTTTATTTTCT

AATGTTATTGCAATAGCTCGGTATAATGTAACCATGTTACTAGCTTAAGATGGTTAGGGTTT

CCCACTTAGGATGTATGAAATATCGCATTGGAGCATCTCCAGCAAGCCATTTTTTTGACGGT

TAACAGCAGGAGCTCTGCTTTTCATTATAGGAGAGGGAAATGCTGTACAGACTGAAGTCAGT

CAGAGCAAAGTAACTTAGAATCATTTATGGGCCACCCTGCACAGGGCAGAAGGCAGGCAGGA

ACGATCCTCTACAGCCGTCGGATTGCCTCCATCAGAGGAATCCTGGCCGTTAATCATGCTCT

GGCCCAGTGGTCAGAATGCATCAACCAGACTGAGGTGCTCGCCTCCTTATTGGTAAAGGATG

CAGCGGTACGAGCCTATTGAACAGATCCTGTTCAAGTAAGGCCGTTCTCCAGCAAGCCATTT

CCTAGCTTATTAATGAGAGAGAGAGAGGGGGGGGGTCTGTATTCTGCGAGCAATTCAAAAAC

TTCCATTGTTCTGAGGTGTACGCATTGTAGGGATCTCCCATTATGAAGAGGATATAGTTAAT

TCTTTGTAACCTACTTGGAAACTTGAGTCTTGCGGCATCGCTAATATATTCTATCATCACAA

TACTTAGAGGATGCATCTGAATATTTTAGTGGGATCTTGCACAGGAACCGAAGATAAATTCA

TATGCTAATTTTAGGGATGAGGTGCTGCCAAGAATTAAAAGGCTTGGATACAATGCAGTGCA

GATAATGGCAATCCAGGAGCATTCATACTATGCGAGCTTTGGGTATTCACACAATCCATTTT

TTTCTGTTCTTTTTTCTGTATGCGCCTCTTCACCCATTTGGAGCTATTACATCCTAATGCTT

CGTGCACATAGAATATTTGGATATAATTCTTTAGTAGACATATAGTACAACAACAGTTGGTA

TTTCTGACTTGTATGACCATTTTATTGTTGTTGGCTTGTTCCAGGTACCATGTTACTAATTT

TTTTGCACCAAGTAGCCGTTTTGGAACTCCAGAGGACTTAAAATCCCTGATCGATAGAGCAC

ATGAGCTTGGTTTGCTTGTTCTTATGGATATTGTTCATAGGTAAGTAGTCCAATTAATTTTA

GCTGCTTTACTGTTTATCTGGTATTCTAAATGGCAGGGCCGTATCGACGAGTATTTTTCCAT

TCTATATAATTGTGCTACATGACTTCTTTTTTCTCAGATGTATTAAACCAGTTGGACATCAA

ATGTATTTGGTACATCTAGTAAACTGACAGTTTCAAAAGAACATCGTTTTGTAATGGCAACA

TGATTTGATGCCATAGATGTGGACTGAGAAGTTCAGATGCTATCAAGAAAATTAATCAACTG

GCCATGTACTCGTGGCACTACATAGAGTTTGCAAGTTGGAAAACTGACAGCAATACCTCACT

GATAAGTAGCTAGGCCCCACTTGCCAGCTTCATATTAGATGTTACTTCCCTGTTGAACTCAT

TTGAACATATTACTTAAAGTTCTTCATTTGTCCTAAGTCAAACTTCTTTAAGTTTGACCAAG

TCTACTGAAAAATATATCAACATCTACAACACCAAATTGGTTTCATTAGATTCACAATTTTT

ATTTTGTTATATTAGCACACCTTTGATGTTGTAGATATCAGCACATTTTTCTACAGACTTGG

TCAAATATAGAGAAGTTTGACTTAGGACAAATCTAGAACTTCAATCAATTTGGATCAGAGGG

GATAGTCCATACTGGTTGATTATATTCGGTAACATCAAATAATATAGATAGATGTCAACACT

TTAACAAAAAAATCAGACCTTGTCACCAAATATGTATCAGACCATCTGTTTGCTTTAGCCAC

TTGTTTTCATATTTATGTGTTTGTACCTAATCTATTTTTACTTCTACTTGGTTTGGTTGATT

TTTTTTCAGTTGCATTGCTTCATCAATGATTTTGTGTACCCTGCAGTCATTCATCAAATAAT

ACCCTTGACGGCTTGAATGGTTTCGATGGCACTGATACACATTACTTCCACGGTGGTCCACG

TGGCCATCATTGGATGTGGGATTCTCGTCTATTCAACTATGGGAGTTGGGAAGTATGTAGCT

CTGACTTCTGTCACCATATTTGGCTAACTGTTCCTGTTAAATCTGTTCTTACACATGTCGAT

ATTCTATTCTTATGTAGGTATTGAGATTCTTACTGTCAAACGCGAGATGGTGGCTTGAAGAA

TATAAGTTTGATGGATTTCGATTTGATGGGGTGACCTCCATGATGTATACTCACCATGGATT
```

-continued

```
ACAAGTAAGTCATCAAGTGGTTTCAGTAACTTTTTTAGGGCACTGAAATAATTGCTATGCAT

CATAACATGTATCATGATCAGGACTTGTGCTACGGAGTCTTAGATAGTTCCCTAGTACGCTT

GTACAATTTTACCTGATGAGATCATGGACGATTCGAAGTGATTATTATTTATTTTTCTTCTA

AGTTTGCTTCTTGTTCTAGATGACATTTACTGGGAACTATGGCGAGTATTTTGGATTTGCTA

CTGATGTTGACGCGGTAGTTTACTTGATGCTGGTCAACGATCTAATTCATGGACTTTATCCT

GATGCTGTATCCATTGGTGAAGATGTAAGTGCTTACAGTATTTATGATTTTTAACCAGTTAA

GTAGTTTTATTTTGGGATCAGGCTGTTACTCTTTTTGTTAGGGGTAAGATCTCTCTTTTCAT

AACAATGCTAATTTATACCTTGTATGATAATGCATCACTTAGGTAATTTGAAAAGTGCAAGG

CCATTCAAGCTTACGAGCATATTTTTTGATGGCTGTAATTTATTTGATAGTATGCTTGTTTG

GGTTTTTCAGTAAATGGGAGTGTGTGACTAATGTTGTATTAGAAATGGGCAACCTTGTCAAT

TGCTTCAGAAGGCTAACTTAGATTCCGTAAACGCTTCAGAAATGAGAGGCTATTCCCATGGA

CATGAAATTATACTTCAGTGTGTTCTGTACATGTATTTGTAAGAGCAAGAGCAACATGGTTT

AACTTAAATTCCTGCACTGCTATGGAATCTCACTGTATGTTGTTAGTGTAACATCCGCAAAC

AAGTAATCCTGAGCTTTCAACTCATGAGAAAATATGAGGTTCCACTTCTGCCAGCATTAACT

GTTCACAGTTCTAATTTGTGTAACTGTGAAATTGTTCAGGTCAGTGGAATGCCCACATTTTG

CATCCCTGTTCCAGATGGTGGTGTTGGTTTTGACTATCGCTTGCATATGGCTGTAGCAGATA

AATGGATTGAACTCCTCAAGTAAGTGCAGGAATATTGGTGATTACATGCGCACAATGATCTA

GATTACAATTTCTAAATGGTAAAAGGAAAATATGTATGTGAATATCTAGACATTTTCCTGTT

ATCAGCTTGTATACGAGAAGTCATACATGGTTTAAATAGCAAATCTCAGAAATGTAATGGCT

AGTGTCTTTATGCTGGACATTGTACATTGCGCTGTAGCAGGCCAGTCAACACAGTTAGCAAT

ATTTTCAGAAACAATAATTATTTATATCCGTATATGGGGAAAGTAGGTATATAAACTGTGGT

CATTAATTGTGTTCACCTTTTGTCCTGTATAAGCATGGGCAGTAGGTAATAAATTTAGCCAG

ATAAAATAAATCGTTATTAGGTTTACAAAAGGAATATACAGGGTCATGTAGCATATCTAGTT

GTAATTATTGAAAAGGCTGACAAAAGGCTCGGTAAAAAAAATCCAGATACGCAGGAACGCGA

CTAAAGCTCAAATATTTATAGTGGTCTCTGTTGCTTGCTGTATATTTGTATCTGCACATATA

TGAAATTACTACTACACAGCTGCCAATCTGTCATGATCTGTGTTCTGCTTTGTGCTATTTAA

ATTTTAATTCGATACATTGGCAATAATAAACTTAACTATTCAACCAATTTGGTGGATACCAG

AGATTTCTGCCCTCTTTTCGTAATGTTGTGCTCCTGCTGCTGTTCTCTGCTGTTACAAAAGC

TGTTCTCAGTTTTTTTACATCATTATTTTTGTGTGTGAGTACTTTTAGCATGTTTTTCGAAG

CTGTGAGTTGTTGGTACTTAATACATTCTTGGTAGTGTCCAAATATGCTGCAGTCTAATTTA

GCATTTCTTTAACACAGGCAAAGTGACGAATCTTGGAAAATGGGTGATATTGTGCACACCCT

AACAAATAGAAGGTGGCTTGAGAAGTGTGTAACTTATGCAGAAAGTCATGATCAAGCACTAG

TTGGTGACAAGACTATTGCATTCTGGTTGATGGATAAGGTACTAGCTGTTACTTTTGGACCA

AAAGAATTACACAATTGATTTGTCTCATCAGATTGCTAGTGTTTTCTTGTGATAAAGATTGG

CTGCGTCACCCATCACCAGCTATTTCCCAACTGTTACTTGAGCAAAATTTGCTGAAAACGTA

CCATGTGGTACTGTGGCGGCTTGTGAACTTTGACTGTTATGGTGCAAATTTCTGTTCTTATT

TTTTTGATTGCTTATGTTACCGTTCATTTGCTCATCCCTTTCAGAGACCAGCCAAAGTCACG

TGTAGCTGTGTGATCTATTATCTGAATCTTGAGCAAATTTTATTAATAGGGTAAAACCCAAC

GAATTATTTGCTTGAATTTTAATATACAGACGTATAGTCACCTGGTGCTTTCTTAAATGATT

ACCATAGTGCCTGAAGGCTGAAATAGTTTTGGCGTTTCTTGGACGCCGCCTAAAGGAGTGAT

TTTGGGTAGATTCCTGGTCGAGCCCTCGTTACAACATACATTTTGGAGATATGCTTAGTAAC
```

-continued

```
TGCTCTGGGAAGTTTGGTCAGAAGTCTGCATCTACACGCTCCTTGAGGTTTTATTATGACGC

CATCTTTGTAACTAGTGGCAGCTGTAAGGAAACACATTCAAAAGGAAACGGTCACATTATTC

TAGTCAGGACCACCACACTAAGAGGAATATTCTGTTCCAATTTTATGAGTTTTTGGGACTCC

AAAGGGAACAAAAGTGTCTCATATTGTGCTTATAACTACAGTTGTTTTTATACCAGTGTAGT

TCCATTCCAGGACAGTTGATACTTGGTACTGTGCTGTAAATTATTGATCTGGCATAGAACAG

CATGAACATATCAAGCTCTCTTTGTGCAGGATATGTATGATTTCATGGCTCTGGATAGGCCT

TCAACTCCTCGCATTGATCGTGGCATAGCATTACATAAAATGATCAGGCTTGTCACCATGGG

TTTAGGTGGTGAAGGCTATCTTAACTTCATGGGAAATGAGTTTGGGCATCCTGGTCAGTCTT

TACAACTTTAATTGCATTCTGCATAGTTGTGATTTACTGTAATTTGAACCATGCTTTGTTTT

CACATTGTATGTATTATGTAATCTGTTGCTTCCAAGGAGGAAGTTAACTTCTATTTACTTGG

CAGAATGGATAGATTTTCCAAGAGGTCCGCAAACTCTTCCAACCGGCAAAGTTCTCCCTGGA

AATAACAATAGTTATGATAAATGCCGCCGTAGATTTGATCTTGTAAGTTTTAGCTTAGCTAT

TACATTTCCTCACTAGATCTTTATCGGCCATTTATTTCTTGATGAAATCATAATGTTTGTTA

GGAAAGATCAACATTGCTTTTGTAGTTTTGTAGACGTTAACATAAATATGTGTTAAGAGTTG

TTGATCATTAAGAATATCATGATTTTTTGTAGGGAGATGCAGATTTTCTTAGATATCGTGGT

ATGCAAGAGTTCGATCAGGCAATGCAGCATCTTGAGGAAAAATATGGGGTATGTCACTGGTT

TGTCTTTGTTGCATAACAAGTCACAGTTTAACATTAGTCTCTTCAAATGGTCAAAAAGTGT

AGAATTAATTTCTGTAATGAGATGAAAACTGTGCAAAGGCGGGAGCTGGAATTGCTCTTCAC

CAATTAAAACTATTTTCTTGAGCGATAGTGTATTGATACCTATACCAACACTGACAATGTAA

CTGCAGTTTATGACATCTGAGCACCAGTATGTTTCACGGAAACACGAGGAAGATAAGGTGAT

CATCTTCGAAAGAGGAGATTTGGTATTTGTTTTCAACTTCCACTGGAGCAATAGCTTTTTTG

ACTACCGTGTTGGGTGTTCCAGGCCTGGGAAGTACAAGGTATGCTTTGCTTTTGCATTGTCC

ACCCTTCACCAGTAGGGTTAGTGGGGCTTCTACAACTTTTAAGTCCACATGTATAGAGTTT

GTTGGTCGTGCAGCTATCAATATAAAGAATATGATAATTTGTAAAGAAAAGAATTTGTTGCT

CGAGCTGTTGTAGTCATATAACATCCCCGAAGCACATCTACTATTCATTCATATTATCTACT

TAAGGGTTTGTTACAATCTTTGTACTCAGTTGGACTCACTCTAATACTGGAACTGTTTACCG

AATCTACCCTAATCATCCTAGCAGTTTTAGAGCAGCCCCATTTGGACAGTCCACTGGGTTTA

GTTGGTTTGTGACAGTTTCTGCTATTTCTTATCAGGTGGCCTTAGACTCCGACGATGCACTC

TTTGGTGGATTCAGCAGGCTTGATCATGATGTCGACTACTTCACAACCGTAAGTCTGGGCCC

AAGCGTTACTTGACTCGTCTTGACTCAACTGCTTACAAATCTGAATCAACTTCTCATTTGCT

GATGCCCTTGCAGGAACATCCGCATGACAACAGGCCGCGCTCTTTCTCGGTGTACACTCCGA

GCAGAACTGCGGTCGTGTATGCCCTTACAGAGTAA
```

The sequence of SEQ ID NO:1 is from the *T. aestivum* (cultivar Chinese Spring) SBEIIa gene within the A genome (GENBANK® accession HE591389.1). Bold nucleotides indicate exon 2 and exon 3 sequences.

A representative example of a naturally occurring *T. aestivum* SBEIIa nucleotide sequence from the B genome is shown in SEQ ID NO:5081:

(SEQ ID NO: 5081)

GTTGGTTTGCGATCCCGTCCTCCCTCCCGTCCCCTACGCAACGTCGCCTCCACCGTCCATCC

GTCGCTGCCACCTCTGTGCGCGCGCACGAGGGAGGAAGACGACGCAGCACACACACTCTCCC

CGTGGGTCCCCTTTCCGGCTTGGCGTCTATCTCCTCTCCCCCCCATCCCCATGCACTGCACA

GTACCCGCCAGCTTCCACCCCCGCCGCACACGTTGCTCCCCCTTCTCATCGCTTCTCAATTA

-continued

ATATCTCCATCACTCGGGTTCCGCGCTGCATTTCGGCCGGCGGGTTGAGTGAGATCTGGGCC

ACTGACCGACTCACTCGCTGCGCGGGGATGGCGACGTTCGCGGTGTCCGGCGCGACCCTCGG

TGTGGCGCGGCCCGCCAGCGCCGGCGGCGGACTGCTGCGATCCGGCTCGGAGCGGAGGGGCG

GGGTGGACTTGCCGTCGCTGCTCCTCAGGAAGAAGGACTCCTCTCGTACGCCTCGCTCCCTC

CAATCTCCCCGTCTGTTTTTGGGCCCCCTTCTCTCTCCCTCGCCTCTCTGCGCGCGCATGGC

CTGTTCGATGCTGTTCCCCAGTTGATCTCCATGAACGAGAGAGATAGCTGGATTAGGCGATC

GCCTCAGGCCCTGGTGTTACCACGGCTTTGATCATCTCCTCCTTTCATGCTGATATTTTCTC

ACTCTTTCTTCTGTTCTTGCTGTAACTGCAAGTTGTAGCATTTTTTTGGCGAATAAGTTGTA

GCATTGTCTCACTATTGTACTCATCCTTGCATTTGCAGGCGCCGTCCTGAGCCGCGCGGCCT

CTCCAGGGAAGGTCCTGGTGCCTGACGGTGAGAGCGACGACTTGGCGGCCACTCCAGCGCAA

CCCGAAGAATTACAGGTACACACCGTCGTGCCGGAAAATCTTCATGCACCCGTTATTCACTT

ACCAAATATCGGATGAACCAAGCCGCGGAGGCATCAGGTTTCAAGCTTCTTCTATCAGCATT

GTGCACTACTTCACTGCCTTGTGCAGTTTGTTAGCTGTGGCCCCGCGCTGGCTCTTGGGCCA

CTGAAAACTCAGATGGATGTGCATTCTAGCAAGAACTTCACAAAATAATGCACTGTTTGTGG

TTTCGTTAGTCTGCTCTACAATTGCTATTTTTCGTGTGCTGTAGATACCTGAAGATATCGAG

GAGCAAACGGCTGAAGTGAACATGACAGGGGGGACTGCAGAGAAACTTCAATATTCAGAACC

GACTCAGGGCATTGTGGAAACAATCACTGATGGTGTAACCAAAGGAGTTAAGGAACTAGTCG

TGGGGGAGAAACCGCGAGTTGTCCCAAAACCAGGAGATGGGCAGAAAATATACGAGATTGAC

CCAACGCTGAAAGATTTTCGGAGCCATCTTGACTACCGGTAATGCCTACCCGCTAATTTCGC

TCATTTTGAATTAAGGTCCTTTCATCATGCAAATTTGGGGAACATCAAAGAGGCAAAGACTA

GGGACCACTGTTTCATACAGTTCCCCTCATGGTCTGAGAATATGCTGGGAAGTATATGTATA

ATTGCTGGCTACAATTGGCTCATAATTGCAATACAAATAACTGTCTCCGATCATTACAATTA

CAGAGTGGCAAACTGATGAAAATGTGGTGGATGGGTTATGGATTTTACTTTGCTAATTCCTC

TACCAAATTCCTGGGGAAAAAATCTACCAGTTGGGCAACTTAGTTTCTTATCTTTGTTGCCT

TTTTGTTTTGGGGAAAACACACTGCTAAATTTGAATGATTTTGGGTATGCCTTGGTGGATTC

AACAGATACAGCGAATACAAGAGAATTCGTGCTGCTATTGACCAACATGAAGGTGGATTGGA

AGCATTTTCTCGTGGTTATGAAAAGCTTGGATTTACCCGCAGGTAAATTTAAAGCTTTACTA

TGAAACGCCTCCACTAGTCTAATTGCATATCTTGTAAGAAAATTTATAATTCCTGTTTTCCC

CTCTCTTTTTTCCAGTGCTGAAGGTATCATCTAATTGCTTATCTTATAAGAAAATTTATAAT

TCCTGTTTCCCCCCCTCTTTTTCCAGTGCTGAAGGTATCACTTACCGAGAATGGGCTCCTGG

AGCGCATGTACGTCTTAACAGACACCTTCTAATCTATTGTTAATGGTCACTATTCACCAACT

AGCTTACTGAACTTACAAAATAGCTTACTGAATACTGACCAGTTACTCTAAATTTATGATCT

GGCTTTTGCATCCTGTTACAGTCTGCAGCATTAGTAGGTGACTTCAACAATTGGAATCCAAA

TGCAGATACTATGACCAGAGTATGTCTACAGCTTGGCAATCTTCCACCTTTGCTTCGTAACT

ACTGATACATCTATTTGTATTTATTTAACTGTTTGCACGTTCGTTAAAGTTGAGCCTCAACT

ATATCATACCAAAATGGTATAATTTGTCAGTGTCTTAAGCTTCAGCCTAAAGATCCTACTGA

ATTTAGTCCATCCTTTTGAGATTGAAAATGAGTATATTAAGGGTGATTGAATACTTGCAACA

CTCCCATTTTTTGGTAGAACCTTTTGCATTATGTGTGCTTTTCCATCCACAATGAGCATATT

TCCATGTTATCAGTGAAGGTTTGCTCCTATTGATGCCGATATTTGATATGATCTTTCGATCT

TTTCAGGATGATTATGGTGTTTGGGAGATCTTCCTCCCTAACAATGCTGATGGATCCCCAGC

-continued

```
TATTCCTCATGGCTCACGTGTAAAGGTAATCTGGCCAATTATTTAGTCGAGGATGTAACATT

TTCGAACTCTGCCTACTAAGGGTCCCTTTTCCTCTCTATTTTCTAGATACGGATGGATACTC

CATCTGGTGTGAAGGATTCGATTTCTGCTTGGATCAAGTTCTCTGTGCAGGCTCCAGGTGAA

ATACCATTCAATGGCATATATTATGATCCACCTGAAGAGGTAAGTATCAATCTATGTTACAT

TATTAAATGGAATTTCCAGTGTTACAGTTTTTGATACCCACTTCATGTCTCACTGACATGT

GAGTCAAGACAATACTTTCGAATTTGGAAGTGACATATGCATTAATTCACCTTCTAAGGGCT

AAGGGGCAACCAACCATGGTGATGTGTGTATGCTTGTGTGACTTAAGATCTTATAGCTCTTT

TATATGTTCTCTGTTGGTTAGGACATTCCATTTTGACCTTTTGTGACCATTTACTAAGGATA

TTTTACATGCAAATGCAGGAGAAGTATGTCTTCCAACATCCTCAACCTAAACGACCAGAGTC

ACTAAGGATTTATGAATCACACATTGGAATGAGCAGCCCGGTATGTCAATAAGTTATTTCAC

CTGTTTCCGGTCTGATGGTTTATTCTATGGATTTTCTAGTTCTGTTATGTACTGTTAACATA

CCACACGGTGCATTCACGTGACAACCTCGATTTTATTTTCTAATGTCTTCATATTGGAAAAT

GCACAACTTTGCTTCCTCTTTGTCTGATCGTTTTTTTGTCTCTAAGATTTCCATTGCATTTC

GAGGTAGCGGGCATGTGAAAGTCGAATCTGAATATTTTTGTCAGAGCACAGTTATATTAAA

TGCCATTGTTGTTGCAATAGCTTGGTATAATGTAGCCATGTTACTAGCTTAAGAAATATCGC

ATTGGAGCATCTCCAGCAAGCCATTTCCTACCTTATTACTNNNNNNNNNNNNNNNNNNNNNN

NNNNNNNNNNNNNNNNNNNNNNNNNNNNNNNNNNNNNNNNNNNNNNNNNNNNNNNNNNNNNN

NNNNNNNNNNNNNNNNNCTGAATATTTTAGCGTGATCTTGCACAGGAACCGAAGATAAATTCA

TATGCTAATTTTAGGGATGAGGTGCTGCCAAGAATTAAAAGGCTTGGATACAATGCAGTGCA

GATAATGGCAATCCAGGAGCATTCATACTATGCAAGCTTTGGGTATTCATACAGTCCATCTT

TTTCTGTTTTTTTTTCTGTATGTGCCTCTTCACCCATTTCGAGCCATTACATCCTAATGCT

TCGTGCACATAAAATACTTGGATATAATTCTTTATTAGACATATAGTACAACACCACTTAGT

ATTTCTGACTTGTATGATCATTTTATTGTTGTTGGCTTGTTACAGGTACCATGTTACTAATT

TTTTTGCACCAAGTAGCCGTTTTGGAACTCCAGAGGACTTAAAATCCTTGATCGATAGAGCA

CATGAGCTTGGTTTGCTTGTTCTTATGGATATTGTTCATAGGTAATCAGTCCAATTTAATTT

TAGTTGCTTTACTGTTTATCTGGTATTGTAAATGGCAGGGCCCTATCGTCGAATATTTTCC

AATCTATATAATTGTGCTACATGACTTATTTTTTCTCAGATGTATTAAACCAGTTGGATATT

AAATGTATTTGGTACATCTAGTAAACTGACAGTTTCATAGAATTGTGTTGTAATGGCAACAC

AATTTGATGGCATAGATGTGGACTGAGAAGTTCAGATGCTATCAGTAATTAATTAACTGGCC

ATGTACTCGTGGAACTACATAGAGTTTGCAAGTTGGAAAACTGACAGCAATACCTCACTGAT

AAGTGTCCAGGCCACACTTGCCAGCTTCATATTAGATGTTACTTCCCTGTTGAACTCCTTTG

AACATATCACTTAAAGTTCTTCAATTGTCCTAAGTCAAACTTCTTTGACTTTGGCCAAGTCT

ATTGAAAAATATGTCAACATCTACAGCACCAAATTAGTTTCATAATTTTTATTTTGTTATAT

TAGCACGTTTTTTATGCTGTAGATATCAGCACATTTTTCTATAGACTTGGTCAAATATAGAG

AAGTTTGACTTAGGACAAATCAGAACTTCAAGCAATTTGGATCAGAGGGAATAGTCCATACT

GCTTGATTATATTTTCCCAAAGGAGGGAGTGAGGAGCTTGACTTCGGTATCATCAAATGATA

TTGATAGATGTCAACATTTTAACAAAAAATCAGACCTTGTCACCAAATATGCATCAGACCAT

CTGTTTGCTTAGGCACTTGCTTTCATATTTATGTGTTTGTAACTAATCTACTTTTCCTTCTA

CTTGGTTTGATTGATTCTATTTCAGTTGCATTGCTTCATCAATGATTTTGTGTACCCTGCAG

TCATTCGTCAAATAATACCCTTGACGGTTTGAATGGTTTCGATGGCACTGATACACATTACT

TCCACGGTGGTCCACGTGGCCATCATTGGATGTGGGATTCTCGTCTGTTCAACTATGGGAGT
```

-continued

```
TGGGAAGTATGTAGCTGCGACTTCTGTCACCATGTTTGGCTAACTGTTCCTGCCAATCTGTT

CTTACACGTGTCAATATTCTATTCTTATACAGGTATTAAGATTCTTACTGTCAAACGCGAGA

TGGTGGCTTGAAGAATATAAGTTTGATGGATTTCGATTTGATGGGGTGACCTCCATGATGTA

TACTCACCATGGATTACAAGTAAGTCATCAAGTGGTTTCAGTAACTTCTTCAGGGCACTGAA

ACAATTGCTATGCATCATAACATGTATCATGATCAGTACTTATGCTACGGAGTCTTAGATAG

TTCCCTAGTATGCTTGTACAATTTTACCTGATGAGATCATGGAAGATTGGAAGTGATTGTTA

TTATTTTTCCTTCTAAGTTTGCTTCTTGTTCTAGATGACATTTACTGGGAACTATGGCGAGT

ATTTTGGATTTGCCACTGATGTTGATGCGGTGGTATACTTAATGCTGGTCAACGATCTAATT

CATGGACTTTATCCTGATGCTGTATCCATTGGTGAAGATGTAAGTGCTTACAGTATTTATGT

TTTTTAACCAGTTAATTTAATAGTATTTTATTTTGGGGATCAAGCTGTTACTACTCTTTTTG

TTAGGGTAAAATCTGTCTTTTCATAAGAATGCTAATTTATACTCCCTCCGTCTGGAAATACT

TGTCGGAGGAATGAATGTATCTAGACGTATTTTAGTTCTAGATACATCCATTTTTATGCATT

TCTCCGTCAAGTATTTCCGGACGGAGGGAGTACCTTGTATGGTAATGCATCACATAGGTAAT

TTGAGAAGTGCAAGGGCATTCAAGCTGACAAGCATATTTGTTGATGGCTGTAATTTATTTGA

TAGTATGCTTGTTTGGATTTTTCAGTAAGTGTGAGTGTGTGAGTAATGTTATATTATTTATT

TACTTGCGGAAGAAATGGGCAACCTTGTCAATTGCTTCAGAAGACTAACTTAGATTCCATAA

ATGCTGTGGAAATGAGAGGCTATTCCCAAGGACACGAAATTATACGTCAGTGTGTTACGCAC

ATGTATTTGTAAGAGCAAGAGCAACATGGTTTAACTTAAATTCCTGCACTGCTATGGAATCT

CACTGTATGTTGTTAGTGTACGCATCCACAAACAAGTAATCCTGAGCTTTCAACTCACGAGA

AAATAGGAGGCTCCACTTCTGCCAGCATTAGCTGTTCACAGTTCTAATTTGTGTAACTCTGA

AATTGTTCAGGTCAGTGGAATGCCTACATTTTGCATCCCTGTTCCAGATGGTGGTGTTGGTT

TTGACTATCGCCTGCATATGGCTGTAGCAGATAAATGGATCGAACTCCTCAAGTAAGTGCAG

GAATATTGGTGATTACATGCGCACAATGATCTACTCCCTCTGTCCCATAATGTAAGATGTTT

TTTGACACTAGTGTAGTGTCAAAAAACGTCCTATATTATGGGAAGGAGGGAGTAGTTCACAA

TTTCTAAATTGTAAAAGAAAAATATGTATGTGAATAGCTAGACATTTCCCTGGTATCAGCT

TCAACACAAGAAGATTTATCAAATACATGATTTAAATAGCAAATTTCGGAAATGTAATGGCT

AGTGTCTTTATGCTGGATATTGTACATGGCGCTGTAGCAGGTGAGTCAATAAAGCTAGCGAT

ATTTTCAGAAACAAAATAATCATTTATATCTGTATATGGGGAAAGTGGGGGTATAGATGGTG

GTCATTAATCGTGTTCACTTTTTGTCCTGTATAAGCACAGGCAGTAGGTAATAAATTTAGCC

AGATAAAATAAATCGTTATTAGGTTTACAAAAGGAATACAGAGGGTCATGTAGCATATCTAG

TTGTAGTTATTGTAAAGGCTGACAAGAGGTTCAGTAAAAAAAACTTTATGTTGATCCCGGGT

ATGCAAGAACGCGAGTAAAGCTCAAACATTTATAGTGGTTGCTGTTGCTTGCTGTATACTTG

TATCTGCGCATATATGAAATTACTACTACACAGCTGCCAATCTGCCATGATCTGTGTTTTGC

TTTGTGCTATTTAAATTTTAAATGCTAACTCAATAAATGGCAATAATAAACTAACTATTCAA

CCAATTTGATGGATATCAGAGATTTCTTCCCTCCTTTAGTAACATTGTGCTCCTGCTGCTGT

TCTCTACCGTTACAAAAGCTGTTTTTCCATTTTTCGCATCATTATTTTTGTGTGTGAGTAAT

TTAAGCATGTCCTTTGAAGCTGTGAGCTGTTGGTACTTAGTACATTCTTGGTAGTGTCCAAA

TATGCTGCAGTCTAATTTAGCATTTCTATAACACAGGCAAAGTGACGAATCTTGGAAAATGG

GCGATATTGTGCACACCCTAACAAATAGAAGGTGGCTTGAGAAGTGCGTCACTTATGCAGAA

AGTCATGATCAAGCACTAGTTGGTGACAAGACTATTGCATTCTGGTTGATGGATAAGGTACT
```

-continued

```
AGCTGTTACTTTTGGATCAAAAGAATCACATAAGATTTGTCTCATCAGATTGCTCATGTTTT
CTTGTGATAAAGATTTGGCCCCCTCACCCATCACCAGCTATTTCCCAACTGTCACTTGAGCA
AAACGTGCCATGTGGCACTGTGGTGGCTTGTGAACTTTGACAGTTAATGTTGCAAATTTCTG
TTCTTATTTATTTGATTCTTATGTTATCGTTCATTTATTCCTCAAAAAATGTTATCGTTCAT
TTGCTCATTCCTTTCCGAGACCAGCCGAAGTCACGTGTAGCCATGTGATCTGCCATCTGAAT
CTTGAGCAAATTTTATGAAGAGGCTAAAGTCGAACGGATTATTTGCTTGAATTTATAAATAT
ACAGACGTATAATCACCTGGTGCTTTCTGAAATGATTACCATAGTGCCTGAAGGCTGAAATA
GTTTTGGCGTTTCCTGGACGACGCCCAAAGGAGTGAATTTTATTGGGTAGATTTCTGGCTGA
GCCCTGGTTACAACATACATTTTGGAGATATGCTTAATAACAAATCTGGGTGTTTGGTCACG
AGTCTGCATCTACATGCTCCTTGGGTTTTATTATGGCGTCATCTTTGTAACTAGTGGCACCC
CTAAGGAAACATTCAAAAGGAAACTGTTACATCATTCTAGTCAGGACCACCGTACTAAGAGC
AAAATTCTGTTCCAATTTTATGAGTTTTTGAGACTCCAAAATGAACATAAGTGTCTCATATT
TTGCTAATTAACTACAGATGTTTTATATCACTTTAGTTTTTATTTCAGGACAGTTGATACT
TGGTACTGTGCTGTAAGCATTGATCCGACACAGAACAGCATGAACATTTCGAGCTCTCTTTG
TGCAGGATATGTATGATTTCATGGCTCTGGATAGACCTTCAACTCCTCGCATTGATCGTGGC
ATAGCATTACATAAAATGATCAGGCTTGTCACCATGGGTTTAGGTGGCGAAGGCTATCTTAA
CTTCATGGGAAATGAGTTTGGGCATCCTGGTCAGTCTTTACAACATTATTGCATTCTGCATG
GTTGTGATTTACTGTAATTTGAACCATGCTTTGTTTTCACATTGTATGTATTATGTAATCTG
TTGCTTCCAAGGAGGAAGTTAACTTCTATTTACTTGGCAGAATGGATAGATTTTCCAAGAGG
TCCGCAAACTCTTCCAACCGGCAAAGTTCTCCCTGGAAATAACAATAGTTATGATAAATGCC
GCCGTAGATTTGATCTTGTAAGTTTTAGCTGTGCTCTTACGTTCCCTCACTAGATCTTTATT
GGCTATTTATTTCTTGATGAAATCATAATGTTTGTTGATCAACATTGCTTTTGTAGTTTTGT
AGACGTTAACATAAATATGTGTTAAGAGTTATTGATCATTAAGAATATCATGATTTTTTTG
TAGGGAGATGCAGATTTTCTTAGATATCGTGGTATGCAAGAGTTCGACCAGGCAATGCAGCA
TCTTGAGGAAAAATATGGGGTATGTCAGTATGTCACTGGTTTGTCTTTGTTGCATAGCAAGT
CACAGTTTAACGCCAGTCTCTTCAAATGGTCAAAAAGTGTAGAATTAATTCCTGTAATGAGA
TGAAAACTGCGCAAAGGCGGGAGCTGGAATTGCTTTTCACCAATTAAAACTATTTTCTTAAG
CGATTGTGTATTGATACCTATACCAACACTGACAATGTAACTGCAGTTTATGACATCTGAGC
ACCAGTATGTTTCACGGAAACATGAGGAAGATAAGGTGATCATCTTCGAAAGAGGAGATTTG
GTATTTGTTTTCAACTTCCACTGGAGCAATAGCTTTTTTGACTACCGTGTTGGGTGTTCCAA
GCCTGGGAAGTACAAGGTATGCTTGCCTTTTCATTGCCCACCCTTCACCAGTAGGGTTAGTG
GGGGCTTCTACAACTTTTAATTCCACATGTAGAGTTTGTTGTTCGTGCAGCTATCAATATAA
AGAATAGGATAATTTGTAAAGAAAAGAATTTGTTGCTCGAGATGTTGTAGTCATATAACATC
CCCGAAGCACATCTACTATTCATTCATATTATCTACTTAAGGGTTTGTTACAATCTTTGTAC
TCAGTTGGACTCACTCTAATACTGGAACTATTTACCGAATCTACCCTAATCATCCTAGCAGT
TTTAGAGCAGCCCCATTTGGACAGTCCACTGGGTTTAGTTGGTTTGTGACAGTTTCTGCTAT
TTCTTAATCAGGTGGCCTTAGACTCCGACGATGCACTCTTTGGTGGATTCAGCAGGCTTGAT
CATGATGTCGACTACTTCACAACCGTAAGTCTGGGCTCAAGCGTCACTTGACTCGTCTAGAC
TCAACTGCTTACAAATCTGAATCAACCTCCCATTTGCTGATGCCCTTGCAGGAACATCCGCA
TGACAATAGGCCGCGCTCTTTCTTGGTGTACACTCCTAGCAGAACTGCGGTCGTGTATGCCC
TTACAGAGTAAGAACCAGCAGCGGCTTGTTACAAGGCAAAGAGAGAACTCCAGGGAGCTCGT
```

-continued

```
GGATTGTGAGCGAAGCGACGGGCAACTGCGTGAGGCTGCTCTAAGCGCCATGACTGGGAGGG

GATCGTGCCTCTTCCCCTGATGCCAGGAGGATCAGATGGATAGGTAGCTTGTTGGTGAGCGC

TCGAAAGAAAATGGACGGGCCTGGGTGTTTGTCGTGCTGCACTTAACCCTCCTCCTATGTTG

CACATTCCCGGGTGTTTTTGTACATATAACTAATAATTGCCCGTGCGCTTCAACATGAACAT

ATAAATATTCTATATAATAGGTTATCCCGTGATTTACCTGCCGATA
```

A representative example of a naturally occurring *T. aestivum* SBEIIa nucleotide sequence from the D genome is shown in SEQ ID NO:5082:

```
                                            (SEQ ID NO: 5082)
CAGCGTCGCCTCCACCGTCCGTCCGTCGCTCTCTGCCACCTCTGCTGTGCGCGCGCACGAGG

GAGGAAGACGACGCCGCACACACACTCACACACGGCACACTCCCCGTGGGTCCCCTTTCCGG

CTCGGCGTCTATCTCCTCTCCCCCGCCCATCCCCATGCACTGCACCGTACCCGCCAGCTTCC

ACCCCCGCCGCACACGTTGCTCCCCCTTCTCATCGCTTCTCAATTAATATCTCCATCACTCG

GGTTCCGCGCTGCATTTCGGCCGGCGGGTTGAGTGAGATCTGGGCGACTGGCTGACTCAATC

ACTACGCGGGGATGGCGACGTTCGCGGTGTCCGGCGCGACTCTCGGTGTGGCGCGGGCCGGC

GTCGGAGTGGCGCGGGCCGGCTCGGAGCGGAGGGGCGGGGCGGACTTGCCGTCGCTGCTCCT

CAGGAAGAAGGACTCCTCTCGTACGCCTCGCTCTCTCGAATCTCCCCGTCTGGCTTTGGCTC

CCCTTCTCTCTCCTCTGCGCGCGCATGGCCTGTTCGATGCTGTTCCCCAATTGATCTCCATG

AGTGAGAGAGATAGCTGGATTAGGCGATCGCGCTTCCTGAACCTGTATTTTTTCCCCGCGG

GGAAATGCGTTAGTGTCACCCAGGCCCTGGTGTTACCACGGCTTTGATCATTCCTCGTTTCA

TTCTGATATATATTTTCTCACTCTTTTTCTTCCTGTTCTTGCTGTAACTGCAAGTTGTGGCG

TTTTTTCACTATTGTAGTCATCCTTGCATTTTGCAGGCGCCGTCCTGAGCCGCGCGGCCTCT

CCAGGGAAGGTCCTGGTGCCTGACGGCGAGAGCGACGACTTGGCAAGTCCGGCGCAACCTGA

AGAATTACAGGTACACACACTCGTGCCGGTAAATCTTCATACAATCGTTATTCACTTACCAA

ATGCCGGATGAAACCAACCACGGATGCGTCAGGTTTCGAGCTTCTTCTATCAGCATTGTGCA

GTACTGCACTGCCTTGTTCATTTTGTTAGCCTTGGCCCCGTGCTGGCTCTTGGGCCACTGAA

AAAATCAGATGGATGTGCATTCTAGCAAGAACTTCACAACATAATGCACCGTTTGGGGTTTC

GTCAGTCTGCTCTACAATTGCTATTTTTCGTGCTGTAGATACCTGAAGATATCGAGGAGCAA

ACGGCGGAAGTGAACATGACAGGGGGGACTGCAGAGAAACTTCAATCTTCAGAACCGACTCA

GGGCATTGTGGAAACAATCACTGATGGTGTAACCAAAGGAGTTAAGGAACTAGTCGTGGGGG

AGAAACCGCGAGTTGTCCCAAAACCAGGAGATGGGCAGAAAATATACGAGATTGACCCAACA

CTGAAAGATTTTCGGAGCCATCTTGACTACCGGTAATGCCTACCCGCTGCTTTCGCTCATTT

TGAATTAAGGTCCTTTCATCATGCAAATTTGGGGAACATCAAAGAGACAAAGACTAGGGACC

ACCATTTCATACAGATCCCCTCGTGGTCTGAGAATATGCTGGGAAGTAAATGTATAATTGAT

GGCTACAATTTGCTCAAAATTGCAATACGAATAACTGTCTCCGATCATTACAATTAAAGAGT

GGCAAACTGATGAAAATGTGGTGGATGGGTTATAGATTTTACTTTGCTAATTCCTCTACCAA

ATTCCTAGGGGGGAAATCTACCAGTTGGGAAACTTAGTTTCTTATCTTTGTGGCCTTTTTGT

TTTGGGGAAAACACATTGCTAAATTCGAATGATTTTGGGTATACCTCGGTGGATTCAACAGA

TACAGCGAATACAAGAGAATTCGTGCTGCTATTGACCAACATGAAGGTGGATTGGAAGCATT

TTCTCGTGGTTATGAAAAGCTTGGATTTACCCGCAGGTAAATTTAAAGCTTTATTATTATGA
```

```
-continued
AACGCCTCCACTAGTCTAATTGCATATCTTATAAGAAAATTTATAATTCCTGTTTTCCCCTC

TCTTTTTTCCAGTGCTGAAGGTATCGTCTAATTGCATATCTTATAAGAAAATTTATATTCCT

GTTTTCCCCTATTTTCCAGTGCTGAAGGTATCACTTACCGAGAATGGGCTCCTGGAGCGCAT

GTATGTCTTTTAAGTCTTAACAGACACCTTCCAATTTATTGTTAATGGTCACTATTCACCAA

CTAGCTTACTGGACTTACAAATTAGCTTACTGAATACTGACCAGTTACTATAAATTTATGAT

CTGGCTTTTGCACCCTGTTACAGTCTGCAGCATTAGTAGGTGACTTCAACAATTGGAATCCA

AATGCAGATGCTATGACCAGAGTATGTCTACAGCTTGGCAATTTTCCACCTTTGCTTCATAA

CTACTGATACATCTATTTGTATTTATTTAGCTGTTTGCACATTCCTTAAAGTTGAGCCTCAA

CTACATCATATCAAAATGGTATAATTTGTCAGTGTCTTAAGCTTCAGCCCAAAGATTCTACT

GAATTTAGTCCATCTTTTTGAGATTGAAAATGAGTATATTAAGGATGAATGAATACGTGCAA

CACTCCCATCTGCATTATGTGTGCTTTTCCATCTACAATGAGCATATTTCCATGCTATCAGT

GAAGGTTTGCTCCTATTGATGCAGATATTTGATATGGTCTTTTCAGGATGATTATGGTGTTT

GGGAGATTTTCCTCCCTAACAACGCTGATGGATCCTCAGCTATTCCTCATGGCTCACGTGTA

AAGGTAAGCTGGCCAATTATTTAGTCGAGGATGTAGCATTTTCGAACTCTGCCTACTAAGGG

TCCCTTTTCCTCTCTGTTTTTTAGATACGGATGGATACTCCATCCGGTGTGAAGGATTCAAT

TTCTGCTTGGATCAAGTTCTCTGTGCAGGCTCCAGGTGAAATACCTTTCAATGGCATATATT

ATGATCCACCTGAAGAGGTAAGTATCGATCTACATTACATTATTAAATGAAATTTCCAGTGT

TACAGTTTTTTAATACCCACTTCTTACTGACATGTGAGTCAAGACAATACTTTTGAATTTGG

AAGTGACATATGCATTAATTCACCTTCTAAGGGCTAAGGGGCAACCAACCTTGGTGATGTGT

GTATGCTTGTGTGTGACATAAGATCTTATAGCTCTTTTATGTGTTCTCTGTTGGTTAGGATA

TTCCATTTTGGCCTTTTGTGACCATTTACTAAGGATATTTACATGCAAATGCAGGAGAAGTA

TGTCTTCCAACATCCTCAACCTAAACGACCAGAGTCACTAAGGATTTATGAATCACACATTG

GAATGAGCAGCCCGGTATGTCAATAAGTTATTTCACCTGTTTCTGGTCTGATGGTTTATTCT

ATGGATTTTCTAGTTCTGTTATGTACTGTTAACATATTACATGGTGCATTCACTTGACAACC

TCGATTTTATTTTCTAATGTCTTCATATTGGCAAGTGCAAAACTTTGCTTCCTCTTTGTCTG

CTTGTTCTTTTGTCTTCTGTAAGATTTCCATNNNNNNNNNNNNNNNNNNNNNNNNNNNNNN

NNNNNNNNNNNNNNNNNNNNNNNNNNNNNNNNNNNNNNNNNNNNNNNNNNNNNNNNNNNN

NNNNNNNGGGGGGGGGGGGGGGGGGGTAGCGTTCTGTATTCTGCGAGCGATTCAAAAACTT

CCATTGTTCTGAGGTGTACGTACTGCAGGGATCTCCCATTATGAAGAGGATATAGTTAATTC

TTTGTAACCTACTTGGAAACTTGAGTCTTGAGGCATCGCTAATATATACTATCATCACAATA

CTTAGAGGATGCATCTGAATATTTTAGTGTGATCTTGCACAGGAACCGAAGATAAATTCATA

TGCTAATTTTAGGGATGAGGTGTTGCCAAGAATTAAAAGGCTTGGATACAATGCAGTGCAGA

TAATGGCAATCCAGGAGCATTCATACTATGCAAGCTTTGGGTATTCACACAATCCATTTTTT

TCTGTATACACCTCTTCACCCATTTGGAGCTATTACATCCTAATGCTTCATGCACATAAAAT

ATTTGGATATAATTCTTTATTAGATATATAGTACAACTACACTTAGTATTCTGACTTTTATG

ATCATTTTATTGTTGTTGGCTTGTTCCAGGTACCATGTTACTAATTTTTTTGCACCAAGTAG

CCGTTTTGGAACTCCAGAGGACTTAAAATCCTTGATCGATAGAGCACATGAGCTTGGTTTGC

TTGTTCTTATGGATATTGTTCATAGGTAATTAGTCCAATTTAATTTTAGCTGTTTTACTGTT

TATCTGGTATTCTAAAGGGAAAATCAGGCAATTATGATACATTGTCAAAAGCTAAGAGTGGC

GAAAGTGAAATGTCAAAATCTAGAGTGGCATAAGGAAAATTGGCAAAAACTAGTGGCAAAAA

TAAAATTTTCCCATCCTAAATGGCAGGGCCCTATCGCCGAATATTTTTCCATTCTATATAAT
```

```
TGTGCTACGTGACTTCTTTTTTCTCAGATGTATTAAACCAGTTGGACATGAAATGTATTTGG

TACATGTAGTAAACTGACAGTTCCATAGAATATCGTTTTGTAATGGCAACACAATTTGATGC

CATAGATGTGGATTGAGAAGTTCAGATGCTATCAATAGAATTAATCAACTGGCCATGTACTC

GTGGCACTACATATAGTTTGCAAGTTGGAAAACTGACAGCAATACCTCACTGATAAGTGGCC

AGGCCCCACTTGCCAGCTTCATACTAGATGTTACTTCCCTGTTGAATTCATTTGAACATATT

ACTTAAAGTTCTTCATTTGTCCTAAGTCAAACTTCTTTAAGTTTGACCAAGTCTATTGGAAA

ATATATCAACATCTACAACACCAAATTACTTTGATCAGATTAACAATTTTTATTTTATTATA

TTAGCACATCTTTGATGTTGTAGATATCAGCACATTTTTCTATAGACTTGGTCAAATATAGA

GAAGTTTGACTTAGGACAAATCTAGAACTTCAATCAATTTGGATCAGAGGGAACATCAAATA

ATATAGATAGATGTCAACACTTCAACAAAAAAATCAGACCTTGTCACCATATATGCATCAGA

CCATCTGTTTGCTTTAGCCACTTGCTTTCATATTTATGTGTTTGTACCTAATCTACTTTTCC

TTCTACTTGGTTTGGTTGATTCTATTTCAGTTGCATTGCTTCATCAATGATTTTGTGTACCC

TGCAGTCATTCGTCAAATAATACCCTTGACGGTTTGAATGGTTTCGATGGCACTGATACACA

TTACTTCCACGGTGGTCCACGCGGCCATCATTGGATGTGGGATTCTCGTCTATTCAACTATG

GGAGTTGGGAAGTATGTAGCTCTGACTTCTGTCACCATATTTGGCTAACTGTTCCTGTTAAT

CTGTTCTTACACATGTTGATATTCTATTCTTATGCAGGTATTGAGATTCTTACTGTCAAACG

CGAGATGGTGGCTTGAAGAATATAAGTTTGATGGATTTCGATTTGATGGGGTGACCTCCATG

ATGTATACTCACCATGGATTACAAGTAAGTCATCAAGTGGTTTCAGTAACTTTTTTAGGGCA

CTGAAACAATTGCTATGCATCATAACATGTATCATGATCAGGACTTGTGCTACGGAGTCTTA

GATAGTTCCCTAGTATGCTTGTACAATTTTACCTGATGAGATCATGGAAGATTGGAAGTGAT

TATTATTTATTTTCTTTCTAAGTTTGTTTCTTGTTCTAGATGACATTTACTGGGAACTATGG

CGAATATTTTGGATTTGCTACTGATGTTGATGCGGTAGTTTACTTGATGCTGGTCAACGATC

TAATTCATGGACTTTATCCTGATGCTGTATCCATTGGTGAAGATGTAAGTGCTTACAGTATT

TATGATTTTTAACTAGTTAAGTAGTTTTATTTTGGGGATCAGTCTGTTACACTTTTTGTTAG

GGGTAAAATCTCTCTTTTCATAACAATGCTAATTTATACCTTGTATGATAATGCATCACTTA

GGTAATTTGAAAAGTGCAAGGGCATTCAAGCTTACGAGCATATTTTTTGATGGCTGTAATTT

ATTTGATAGTATGCTTGTTTGGGTTTTTCAATAAGTGGGAGTGTGTGACTAATGTTGTATTA

TTTATTTAATTGCGGAAGAAATGGGCAACCTTGTCAATTGCTTCAGAAGGCTAACTTTGATT

CCATAAACGCTTTGGAAATGAGAGGCTATTCCCAAGGACATGAATTATACTTCAGTGTGTTC

TGTACATGTATTTGTAATAGTGGTTTAACTTAAATTCCTGCACTGCTATGGAATCTCACTGT

ATGTTGTTAGTGTACACATCCACAAACAAGTAATCCTGAACTTTCAACTCATGAGAAAATAG

GAGGTTCCGCTTCTGCCAGCATTAACTGTTCACAGTTCTAATTTGTGTAACTGTGAAATTGT

TCAGGTCAGTGGAATGCCTACATTTTGCATCCCTGTTCCAGATGGTGGTGTTGGTTTTGACT

ACCGCCTGCATATGGCTGTAGCAGATAAATGGATTGAACTCCTCAAGTAAGTGCAGGAATAT

TGGTGATTACATGCGCACAATGATCTAGATTACATTTTCTAAATGGTAAAAAGGAAAATATG

TATGTGAATATCTAGACATTTGCCTGTTATCAGCTTGAATACGAGAAGTCAAATACATGATT

TAAATAGCAAATCTCGGAAATGTAATGGCTAGTGTCTTTATGCTGGGCAGTGTACATTGCGC

TGTAGCAGGCCAGTCAACACAGTTAGCAATATTTTCAGAAACAATATTATTTATATCCGTAT

ATGAGGAAAGTAGGTATATAAACTGTGGTCATTAATTGTGTTCACCTTTTGTCCTGTTTAAG

GATGGGCAGTAGGTAATAAATTTAGCCAGATAAAATAAATCGTTATTAGGTTTACAAAAGGA
```

-continued

```
ATATACAGGGTCATGTAGCATATCTAGTTGTAATTAATGAAAAGGCTGACAAAAGGCTCGGT

AAAAAAAACTTTATGATGATCCAGATAGATATGCAGGAACGCGACTAAAGCTCAAATACTTA

TTGCTACTACACAGCTGCCAATCTGTCATGATCTGTGTTCTGCTTTGTGCTATTTAGATTTA

AATACTAACTCGATACATTGGCAATAATAAACTTAACTATTCAACCAATTTGGTGGATACCA

GAGATTTCTGCCCTCTTGTAGTAATGATGTGCTCCTGCTGCTGTTCTCTGCCGTTACAAAAG

CTGTTTTCAGTTTTTTGCATCATTATTTTTGTGTGTGAGTAGTTTAAGCATGTTTTTTGAAG

CTGTGAGCTGTTGGTACTTAATACATTCTTGGAAGTGTCCAAATATGCTGCAGTGTAATTTA

GCATTTCTTTAACACAGGCAAAGTGACGAATCTTGGAAAATGGGCGATATTGTGCACACCCT

AACAAATAGAAGGTGGCTTGAGAAGTGTGTAACTTATGCAGAAAGTCATGATCAAGCACTAG

TTGGTGACAAGACTATTGCATTCTGGTTGATGGATAAGGTACTAGCTGTTACTTTTGGACCA

AAAGAATTACTCCCTCCGTTCCTAAATATAAGTCTTTGTAGAGATTCCACTATGGACCACAT

AGTATATAGATGCATTTTAGAGTGTAGATTCACTCATTTTGCTTCGTATGTAGTCCATAGTG

AAATCTCTACAGAGACTTATATTTAGGAACGGAGGGAGTACATAATTGATTTGTCTCATCAG

ATTGCTAGTGTTTTCTTGTGATAAAGATTGGCTGCCTCACCCATCACCAGCTATTTCCCAAC

TGTTACTTGAGCAGAATTTGCTGAAAACGTACCATGTGGTACTGTGGCGGCTTGTGAACTTT

GACAGTTATGTTGCAATTTTCTGTTCTTATTTATTTGATTGCTTATGTTACCGTTCATTTGC

TCATTTCTTTCCGAGACCAGCCAAAGTCACGTGTAGCTGTGTGATCTGTTATCTGAATCTTG

AGCAAATTTTATTAATAGGCTAAAATCCAACGAATTATTTGCTTGAATTTAAATATACAGAC

GTATAGTCACCTGGCTCTTTCTTAGATGATTACCATAGTGCCTGAAGGCTGAAATAGTTTTG

GTGTTTCTTGGATGCCGCCTAAAGGAGTGATTTTTATTGGATAGATTCCTGGCCGAGTCCTC

GTTACAACATACATTTTGGAGATATGCTTAGTAACAGCTCTGGGAAGTTTGGTCACAAGTCT

GCATCTACACGCTCCTTGAGGTTTTATTATGGCGCCATCTTTGTAACTAGTGGCACCTGTAA

GGAAACACATTCAAAAGGAAACGGTCACATCATTCTAATCAGGACCACCATACTAAGAGCAA

GATTCTGTTCCAATTTTATGAGTTTTTGGGACTCCAAAGGGAACAAAAGTGTCTCATATTGT

GCTTATAACTACAGTTGTTTTTATACCAGTGTAGTTTTATTCCAGGACAGTTGATACTTGGT

ACTGTGCTGTAAATTATTTATCCGACATAGAACAGCATGAACATATCAAGCTCTCTTTGTGC

AGGATATGTATGATTTCATGGCTCTGGATAGGCCTTCAACTCCTCGCATTGATCGTGGCATA

GCATTACATAAAATGATCAGGCTTGTCACCATGGGTTTAGGTGGTGAAGGCTATCTTAACTT

CATGGGAAATGAGTTTGGGCATCCTGGTCAGTCTTTACAACATTATTGCATTCTGCATGATT

GTGATTTACTGTAATTTGAACCATGCTTTTCTTTCACATTGTATGTATTATGTAATCTGTTG

CTTCCAAGGAGGAAGTTAACTTCTATTTACTTGGCAGAATGGATAGATTTTCCAAGAGGCCC

ACAAACTCTTCCAACCGGCAAAGTTCTCCCTGGAAATAACAATAGTTATGATAAATGCCGCC

GTAGATTTGATCTTGTAAGTTTTAGCTGTGCTATTACATTCCCTCACTAGATCTTTATTGGC

CATTTATTTCTTGATGAAATCATAATGTTTGTTAGGAAAGATCAACATTGCTTTTGTAGTTT

TGTAGACGTTAACATAAGTATGTGTTGAGAGTTGTTGATCATTAAAAATATCATGATTTTTT

GCAGGGAGATGCAGATTTTCTTAGATATCGTGGTATGCAAGAGTTCGATCAGGCAATGCAGC

ATCTTGAGGAAAAATATGGGGTATGTCACTGGTTTGTCTTTGTTGCATAACAAGTCACAGTT

TAACGTCAGTCTCTTCAAGTGGTAAAAAAAGTGTAGAATTAATTCCTGTAATGAGATGAAAA

CTGTGCAAAGGCGGAGCTGGAATTGCTTTTCACCAAAACTATTTTCTTAAGTGCTTGTGTAT

TGATACATATACCAGCACTGACAATGTAACTGCAGTTTATGACATCTGAGCACCAGTATGTT

TCACGGAAACATGAGGAAGATAAGGTGATCATCTTCGAAAGAGGAGATTTGGTATTTGTTTT
```

-continued

```
CAACTTCCACTGGAGCAATAGCTTTTTTGACTACCGTGTTGGGTGTTCCAAGCCTGGGAAGT

ACAAGGTATGCTTGCCTTTTCATTGTCCACCCTTCACCAGTAGGGTTAGTGGGGGCTTCTAC

AACTTTTAATTCCACATGGATAGAGTTTGTTGGTCGTGCAGCTATCAATATAAAGAATAGGG

TAATTTGTAAAGAAAAGAATTTGCTCGAGCTGTTGTAGCCATAGGAAGGTTGTTCTTAACAG

CCCCGAAGCACATACCATTCATTCATATTATCTACTTAAGTGTTTGTTTCAATCTTTATGCT

CAGTTGGACTCGGTCTAATACTAGAACTATTTTCCGAATCTACCCTAACCATCCTAGCAGTT

TTAGAGCAGCCCCATTTGGACAATTGGCTGGGTTTTTGTTAGTTGTGACAGTTTCTGCTATT

TCTTAATCAGGTGGCCTTGGACTCCGACGATGCACTCTTTGGTGGATTCAGCAGGCTTGATC

ATGATGTCGACTACTTCACAACCGTAAGTCTGGGCTCAAGCGTCACTTGACTCGTCTTGACT

CAACTGCTTACAAATCTGAATCAACTTCCCAATTGCTGATGCCCTTGCAGGAACATCCGCAT

GACAACAGGCCGCGCTCTTTCTCGGTGTACACTCCGAGCAGAACTGCGGTCGTGTATGCCCT

TACAGAGTAAGAACCAGCAGCGGCTTGTTACAAGGCAAAGAGAGAACTCCAGAGAGCTCGTG

GATCGTGAGCGAAGCGACGGGCAACGGCGCGAGGCTGCTCCAAGCGCCATGACTGGGAGGGG

ATCGTGCCTCTTCCCCAGATGCCAGGAGGAGCAGATGGATAGGTAGCTTGTTGGTGAGCGCT

CGAAAGAAAATGGACGGGCCTGGGTGTTTGTTGTGCTGCACTGAACCCTCCTCCTATCTTGC

ACATTCCCGGTTGTTTTTGTACATATAACTAATAATTGCCCGTGCGCTTCAACATGAACATA

TAAATATTCTAATAGGTTATCCCGTGATTTACCTGCCTAT
```

The SBEIIa amino acid sequence encoded by the *T. aestivum* (cultivar Chinese Spring) SBEIIa gene A genome is set forth in SEQ ID NO:2 (GENBANK® accession CCD41775.1):

```
                                           (SEQ ID NO: 2)
MATFAVSGATLGVARPAGAGGGLLPRSGSERRGGVDLPSLLLRKKDSSRA

VLSRAASPGKVLVPDGESDDLASPAQPEELQIPEDIEEQTAEVNMIGGTA

EKLESSEPTQGIVETITDGVTKGVKELVVGEKPRVVPKPGDGQKIYEIDP

TLKDFRSHLDYRYSEYRRIRAAIDQHEGGLEAFSRGYEKLGFTRSAEGIT

YREWAPGAHSAALVGDFNNWNPNADTMTRDDYGVWEIFLPNNADGSPAIP

HGSRVKIRMDTPSGVKDSISAWIKFSVQAPGEIPFNGIYYDPPEEEKYVF

QHPQPKRPESLRIYESHIGMSSPEPKINSYANFRDEVLPRIKRLGYNAVQ

IMAIQEHSYYASFGYHVTNFFAPSSRFGTPEDLKSLIDRAHELGLLVLMD

IVHSHSSNNTLDGLNGFDGIDTHYFHGGPRGHHWMWDSRLENYGSWEVLR

ELLSNARWWLEEYKEDGFREDGVTSMMYTHHGLQMTFTGNYGEYFGFATD

VDAVVYLMLVNDLIHGLYPDAVSIGEDVSGMPTFCIPVPDGGVGFDYRLH

MAVADKWIELLKQSDESWKMGDIVHILTNRRWLEKCVTYAESHDQALVGD

KTIAFWLMDKDMYDFMALDRPSTPRIDRGIALHKMIRLVTMGLGGEGYLN

FMGNEFGHPEWIDFPRGPQTLPTGKVLPGNNNSYDKCRRRFDLGDADFLR

YRGMQEFDQAMQHLEEKYGFMTSEHQYVSRKHEEDKVIIFERGDLVFVFN

FHWSNSFFDYRVGCSRPGKYKVALDSDDALFGGFSRLDHDVDYFTTEHPH

DNRPRSFSVYTPSRTAVVYALTE
```

The *Triticum* plants, cells, plant parts, grains, and progeny thereof that are provided herein have a mutation in at least two endogenous SBEII alleles, such that expression of the SBEIIa or SBEIIb genes is reduced or completely inhibited, or the activity of the SBEIIa enzyme or SBEIIb enzyme is lost. Thus, the plants, cells, plant parts, grains, and progeny exhibit higher levels of amylose.

The term "rare-cutting endonucleases" as used herein refers to natural or engineered proteins having endonuclease activity directed to nucleic acid sequences with a recognition sequence (target sequence) about 12-40 bp in length (e.g., 14-40, 15-36, or 16-32 bp in length). Several rare-cutting endonucleases cause cleavage inside their recognition site, leaving 4 nt staggered cuts with 3'OH or 5'OH overhangs. These rare-cutting endonucleases may be meganucleases, such as wild type or variant proteins of homing endonucleases, more particularly belonging to the dodecapeptide family (LAGLIDADG (SEQ ID NO:3); see, WO 2004/067736), or may be fusion proteins containing a DNA binding domain and a catalytic domain with cleavage activity. TALE nucleases and zinc-finger-nucleases (ZFN) are examples of fusions of DNA binding domains with the catalytic domain of the FokI endonuclease. Customized TALE nucleases are commercially available under the trade name TALEN™ (Cellectis, Paris, France). For a review of rare-cutting endonucleases, see Baker, *Nature Methods* 9:23-26, 2012. Additional rare-cutting endonucleases can be used in the methods disclosed herein are known as "Mega-TAL" nucleases, and include a fusion of a TALE binding domain with a meganuclease (see, e.g., EP3320910 and Boissel et al., *Nucl Acids Res* 42(4):2591-2601, 2014). RNA-guided endonucleases referred to as Cas9 or Cpf1 systems also can be used, as described further below (see, also, Begemann et al., *Scientific Reports* 7:11606, 2017).

"Mutagenesis" as used herein refers to processes in which mutations are introduced into a selected DNA sequence. Mutations induced by endonucleases generally are obtained by a double strand break, which results in insertion/deletion mutations ("indels") that can be detected by deep-sequencing analysis. Such mutations typically are deletions of several base pairs, and have the effect of inactivating the mutated allele. Mutations also can be introduced by generating two double-strand breaks on the same chromosome, resulting in either two indels or the deletion/inversion of intervening sequence. In the methods described herein, for example, mutagenesis occurs via double stranded DNA breaks made by TALE nuclease pairs targeted to selected DNA sequences in a plant cell. Such mutagenesis results in "TALE nuclease-induced mutations" (e.g., TALE nuclease-induced knockouts) and reduced expression of the targeted gene, or reduced activity of the SBEII protein. Following mutagenesis, plants can be regenerated from the treated cells using known techniques (e.g., planting seeds in accordance with conventional growing procedures, followed by self-pollination).

The plants, plant cells, plant parts, grains, and progeny provided herein can be generated using a TALE nuclease system to make targeted mutations in SBEII alleles. Thus, this document provides materials and methods for using rare-cutting endonucleases (e.g., TALE nucleases) to generate *Triticum* plants and related products (e.g., grains and plant parts) that can be used to make flour with high amylose, due to mutations in the SBEII alleles. Other sequence-specific nucleases also may be used to generate the desired plant material, including engineered homing endonucleases, zinc finger nucleases, and RNA-guided endonucleases.

The term "expression" as used herein refers to the transcription of a particular nucleic acid sequence to produce sense or antisense RNA or mRNA, and/or the translation of an mRNA molecule to produce a polypeptide, with or without subsequent post-translational events.

"Reducing the expression" or "reduced expression" of a gene or polypeptide in a plant or a plant cell includes inhibiting, interrupting, knocking-out, or knocking-down the gene or polypeptide, such that transcription of the gene and/or translation of the encoded polypeptide is reduced as compared to a corresponding control plant or plant cell in which expression of the gene or polypeptide is not inhibited, interrupted, knocked-out, or knocked-down. Expression levels can be detected and/or measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

In general, a mutant *Triticum* plant, plant part, or plant cell as provided herein can have its expression of SBEII alleles reduced by more than 60 percent (e.g., by more than 70 percent, more than 80 percent, or more than 90 percent) as compared to a control *Triticum* plant that lacks the mutation(s). The control *Triticum* plant can be, for example, a wild-type *Triticum* plant in which the SBEII alleles have not been mutated.

In some embodiments, a mutant *Triticum* plant, plant part, or plant cell can contain a mutation in an SBEII nucleic acid having a sequence with at least 90 percent identity to a representative SBEII nucleotide sequence. For example, a mutation can be in a nucleotide sequence with at least 91 percent, at least 92 percent, at least 93 percent, at least 94 percent, at least 95 percent, at least 96 percent, at least 97 percent, at least 98 percent, or at least 99 percent sequence identity to a representative, naturally occurring SBEII nucleotide sequence.

In some cases, a mutation can be at a target sequence as set forth in an SBEIIa coding sequence as set forth herein (e.g., SEQ ID NO:1), or at a target sequence that is at least 90 percent (e.g., at least 92 percent, at least 94 percent, at least 96 percent, at least 97 percent, at least 98 percent, or at least 99 percent) identical to the sequence set forth in an SBEIIa sequence as set forth herein (e.g., SEQ ID NO:1).

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 9,500 matches when aligned with the sequence set forth in SEQ ID NO:1 is 96.0 percent identical to the sequence set forth in SEQ ID NO:1 (i.e., 9,500±9,893×100=96.0). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Methods for selecting endogenous target sequences and generating TALE nuclease pairs targeted to such sequences can be performed as described elsewhere. See, for example, PCT Publication No. WO 2011/072246, which is incorporated herein by reference in its entirety. In some embodiments, software that specifically identifies TALE nuclease recognition sites, such as TALE-NT 2.0 (Doyle et al., *Nucleic Acids Res* 40:W117-122, 2012) can be used.

Transcription activator-like (TAL) effectors are found in plant pathogenic bacteria of the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc Natl Acad Sci USA* 103:10503-10508, 2006; Kay et al. *Science* 318:648-651, 2007; Sugio et al., *Proc Natl Acad Sci USA* 104:10720-10725, 2007; and Romer et al. *Science* 318:645-648, 2007). Specificity depends on an effector-variable number of imperfect, typically 34 amino acid repeats (Schornack et al., *J Plant Physiol* 163:256-272, 2006; and WO 2011/072246). Polymorphisms are present primarily at repeat positions 12 and 13, which are referred to as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (i.e., double-stranded breaks) in DNA can induce mutations into the wild type DNA sequence via non-homologous end joining (NHEJ) or homologous recombination, for example. In some cases, TALE nucleases can be used to facilitate site directed mutagenesis in complex genomes, knocking out or otherwise altering gene function with great precision and high efficiency. As described in the Examples below, TALE nucleases targeted to the *T. aestivum* SBEII alleles can be used to mutagenize the endogenous alleles, resulting in plants without detectable expression (or reduced expression) of SBEII. The fact that some endonucleases (e.g., FokI) function as dimers can be used to enhance the target specificity of the TALE nuclease. For example, in some cases a pair of TALE nuclease monomers targeted to different DNA sequences can be used. When the two TALE nucleases recognition sites are in close proximity, the inactive monomers can come together to create a functional enzyme that cleaves the DNA. By requiring DNA binding to activate the nuclease, a highly site-specific restriction enzyme can be created.

Methods for using TALE nucleases to generate *Triticum* plants, plant cells, or plant parts having mutations in endogenous genes include, for example, those described in the Examples herein. For example, one or more nucleic acids encoding TALE nucleases targeted to conserved nucleotide sequences present in one or more SBEII alleles can be transformed into plant cells or plant parts (e.g., protoplasts or scutella), where they can be expressed. In some cases, one or more TALE nuclease proteins can be introduced into plant cells or plant parts (e.g., protoplasts or scutella). The cells or plant parts, or a plant cell line or plant part generated from the cells, can subsequently be analyzed to determine whether mutations have been introduced at the target site(s), through next-generation sequencing techniques (e.g., 454 pyrosequencing or Illumina sequencing). The template for sequencing can be, for example, a TALE nuclease target site within an SBEII gene sequence that is amplified by PCR (e.g., using primers that are homologous to conserved nucleotide sequences across all SBEII alleles).

RNA-guided rare-cutting endonucleases also can be used in the methods provided herein. For example, the clustered regularly interspaced short palindromic repeats/CRISPR-associated (CRISPR/Cas) systems use RNA to direct DNA cleavage (see, e.g., Belahj et al., *Plant Methods* 9:39, 2013). These systems can consist of a Cas9 or Cpf1 (Zetsche et al., *Nature Biotechnol* 35:31-34, 2017) endonuclease and a guide RNA (either a complex between a CRISPR RNA [crRNA] and trans-activating crRNA [tracrRNA], or a synthetic fusion between the 3' end of the crRNA and 5'end of the tracrRNA). The guide RNA directs Cas9 or Cpf1 binding and DNA cleavage to sequences that are adjacent to a proto-spacer adjacent motif (PAM; e.g., NGG for Cas9 from *Streptococcus pyogenes*). Once at the target DNA sequence, Cas9 or Cpf1 generates a DNA double-strand break at a position three nucleotides from the 3' end of the crRNA sequence that is complementary to the target sequence. As there are several PAM motifs present in the nucleotide sequence of the SBEII alleles, the CRISPR/Cas system may be employed to introduce mutations within the SBEII alleles within *Triticum* plant cells in which the Cas9 or Cpf1 endonuclease and the guide RNA are transfected and expressed. This approach can be used as an alternative to TALE nucleases in some instances, to obtain plants and plant parts as described herein.

The present document also provides wheat grain having an altered starch content as compared to the starch content in grain from corresponding wild-type wheat. The term "grain" as used herein refers to essentially mature grain. This includes grain harvested in a commercial setting. In some embodiments, the altered starch content is at least partly a consequence of reduced SBEIIa expression. In some embodiments, the grain has an increased proportion of amylose (as a percentage of total starch). This may be determined as a reduced proportion of amylopectin in the starch, compared to grain from a wild-type plant. Wild-type wheat starch typically contains about 20-30% amylose and 70-80% amylopectin. The grain provided herein can have a starch content that includes at least about 40% (w/w) amylose. In some embodiments, the activities of both SBEIIa and SBEIIb are reduced during development of the endosperm. In some embodiments, the proportion of amylose, as measured by methods understood in the art, for example, can be at least 40%, at least 55%, at least 60%, at least 65%, at least 70%, at least 75%, at least 80%, or at least 90% (w/w) of the total starch of the grain. Increased amylose levels may be evidenced by abnormal starch granule morphology, by loss of birefringence of the granules when observed under a light microscope, or by other suitable methods. In some embodiments, for example, the proportion of amylose can be measured using a potentiometric, amperometric, or colourimetric measurement of the iodine binding capacity of amylose in amylose-iodine inclusion complexes. Amylose content also can be measured by high-performance liquid chromatography (Batey and Curtin, *Starch* 48:338-344, 1996), or by specific precipitation of branched amylopectin with lectin concanavalin A (Con A) (Yun and Matheson, *Starch/Starke* 42:302-305, 1990), followed by colorimetric quantification of D-glucose in hydrolyzed amylose. The colorimetric quantification may include a spectrophotometric method such as, for example, the method of Morrison and Laignelet (*J Cereal Sci* 9-20, 1983).

The term "dietary fiber" as used herein includes the carbohydrate and carbohydrate digestion products that are not absorbed in the small intestine of healthy humans, but that enter the large bowel. This includes resistant starch and other soluble and insoluble carbohydrate polymers. It is intended to include that portion of carbohydrates that are fermentable, at least partially, in the large bowel by the resident microflora. The starch provided herein contains relatively high levels of dietary fiber, more particularly amylose. The dietary fiber content of the grain provided herein results at least in part from the increased amylose content in the starch of the grain, and also, or in combination with, an increased resistant starch content as a percentage of the total starch.

"Resistant starch" (RS) is defined herein as the sum of starch and products of starch digestion that are not absorbed in the small intestine of healthy humans but that enter into the large bowel. This is defined in terms of a percentage of the total starch of the grain, or a percentage of the total starch content in the food, according to the context. Thus, resistant starch excludes products digested and absorbed in the small intestine. Resistant starches include physically inaccessible starch (RSI form), resistant native starch granules (RS2), retrograded starches (RS3), and chemically modified starches (RS4). The altered starch structure and in particular the high amylose levels of the starch from the wheat provided herein give rise to an increase in resistant starch when consumed in food. The starch may be in an RSI form, being somewhat inaccessible to digestion. Starch-lipid association as measured by V-complex crystallinity is also likely to contribute to the level of resistant starch.

This document provides wheat grain with an altered resistant starch content, as a consequence of the increased proportion of amylose. Wild-type wheat seeds contain less than 2% of resistant starch in whole grain. The grain provided herein can have at least about 3%, at least about 4%, at least about 6%, at least about 8%, at least about 10%, at least about 12%, or at least about 14% resistant starch. The proportion of resistant starch can be indirectly measured by, for example, spectrophotometric quantification of D-glucose in hydrolyzed starch with alpha-amylase and pancreatic amyloglucosidase (see, e.g., Official Methods of Analysis of AOAC International (2005), 18th Ed., AOAC International, Gaithersburg, Maryland, USA, Official Method 2002.02).

The present document also provides wheat grain having an altered dietary fiber content as compared to wild type wheat grain. The altered dietary fiber content can be at least partly a consequence of increased amylose content due to reduced SBEIIa expression. Wild-type wheat seeds typically have a dietary fiber content from about 12% to about 15%. The grain provided herein can have a dietary fiber content of at least about 20%, at least about 25%, at least about 30%, or at least about 35% of the whole grain. The proportion of dietary fiber can be measured using, for example, the McCleary fiber method (Official Methods of Analysis of AOAC International, supra, Method 2011.25) for the determination of insoluble, soluble and total dietary fiber, inclusive of RS and dietary fiber that is not precipitated in 4 parts alcohol, 1 part water (SDFS/LMWSDF) with a degree of polymerization (DP)≥3, consistent with the CODEX definition adopted in 2009 (Codex, 2009.01). The proportion of dietary fiber also can be measured using the Lee method (Official Methods of Analysis of AOAC International, supra, Method 991.43).

In some embodiments, as illustrated in the Examples herein, this document provides methods for engineering wheat plants by introducing deletions or insertions into endogenous SBEIIa alleles using one or more rare-cutting endonucleases that specifically bind to at least one of SEQ ID NOS:6-8:

```
                                          (SEQ ID NO: 6)
TTCAGAACCGACTCAGGGCATTGTGGAAACAATCACTGATGGTGTAACC

A,
                                          (SEQ ID NO: 7)
TATACGAGATTGACCCAACGCTGAAAGATTTTCGGAGCCATCTTGACTA, and/or
                                          (SEQ ID NO: 8)
TCCTGAGCCGCGCGGCCTCTCCAGGGAAGGTCCTGGTGCCTGACGGCGA,
``` such that the rare-cutting endonuclease(s) target endogenous sequences encoding SBEII polypeptides that contain at least one of those sequences.

The modified plant cells can be regenerated into whole wheat plants that produce grains, which can be compared with the parental (wild type) plants from which they were derived. The grains resulting from the regenerated plants can be generally characterized by their simultaneous increase in total protein content and amylose content. The total protein content can be increased by about 5 to 20% or more (e.g., at least 5%, at least 10%, at least 15%, or at least 20%) as compared to the total protein content in corresponding wild type wheat. The amylose content (as a percentage of total starch) can be increased by about 5 to 50% or more (e.g., at least 5%, at least 10%, at least 15%, at least 20%, at least 25%, at least 30%, at least 35%, at least 40%, at least 45%, or at least 50%) as compared to the amylose content in wild type wheat. In addition, the amylopectin content (as a percentage % of total starch) can be decreased from about 5 to 40% or more (e.g., at least 10%, at least 15%, at least 20%, at least 25%, at least 30%, at least 35%, or at least 40%) as compared to the amylopectin content in wild type wheat. Further, in some cases, the total starch content can be decreased by about 5 to 20% (e.g., at least 5%, at least 10%, or at least 15%) as compared to the total starch content in wild type wheat.

This document also provides flour, meal, dough, and other products produced from or using the grain provided herein. These products may be unprocessed or processed, for example by fractionation or bleaching. This document further provides wheat grain useful for food production obtained from the wheat plant provided herein. Additionally, this document encompasses grain processed in other ways, so that the grain may have been milled, ground, rolled, pearled, kibbled or cracked, or par boiled (polenta).

The invention will be further described in the following examples, which do not limit the scope of the invention described in the claims.

EXAMPLES

Example 1—Engineering Sequence-Specific Nucleases to Mutagenize SBEIIa Alleles To attenuate or inactivate SBEIIa alleles in *Triticum* plants, sequence-specific nucleases were designed to target conserved nucleotides within the SBEIIa coding sequences. To identify conserved sequences within the SBEIIa homoeoalleles for TALE nuclease binding, partial sequences of the SBEIIa alleles on genomes A, B, and D were amplified by PCR using primers oNJB011 (5'-ACTCCTCTCGTACGCCTCGC; SEQ ID NO:4) and oNJB013 (5'-CCAATCCACCTTCATGTTGGTCA; SEQ ID NO:5). The nucleotide sequences of exons 2 and 3 of the SBEIIa genes are shown in FIG. 1. Numerous SNPs were identified between the SBEIIa-A, B and D homoeoalleles, making TALE nuclease design challenging. Three TALE nuclease target sites were chosen, and there was at least one nucleotide difference between the homoeoalleles at each target site. The predicted binding sites for TALE nucleases TaSBEIIa_T01, TaSBEIIa_T02 and TaSBEIIa_T03 were TATACGAGATTGACCCAACGCTGAAAGATTTTCG-GAGCCATCTTGACTA (SEQ ID NO:7), TTCAGAACCGACTCAGGGCATTGTGGAAACAAT CACTGATGGTGTAACCA (SEQ ID NO:6), and TCCT-GAGCCGCGCGGCCTCTCC AGGGAAGGTCCTGG-TGCCTGACGGCGA (SEQ ID NO:8), respectively. TALE nuclease pairs were synthesized using methods similar to those described elsewhere (Cermak et al., *Nucleic Acids Res* 39:e82, 2011; Reyon et al., *Nat Biotechnol* 30:460-465, 2012; and Zhang et al., *Nat Biotechnol* 29:149-153, 2011). The relative positions of the TALE nuclease target sites in a representative SBEIIa gene are shown in FIG. 2. The predicted nucleotide target sites of the TALE nucleases in each SBEIIa gene are shown in FIG. 3.

Example 2—Activity of SBEIIa TALE Nuclease Pairs at their Endogenous Target Sites in *T. aestivum*

To assess TALE nuclease activity at endogenous target sequences, TALE nuclease pairs are stably integrated into the wheat genome, and target sites are surveyed for mutations introduced by NHEJ. Methods for integrating DNA into the *Triticum* genome either through *Agrobacterium* or biolistics are performed as described elsewhere (Cheng et al., *Plant Physiol*, 115:971-980, 1997; Rasco-Gaunt et al., *J Exp Botany*, 52:865-874, 2000). Transformed cells are placed on selection and regeneration media, and transgenic calli or plantlets are produced. To assess TALE nuclease activity, genomic DNA from transgenic calli or plantlets is extracted using a hexadecyltrimethylammonium bromide- (CTAB-) based method and used as a template for PCR using primers designed to amplify the TALE nuclease target sequence. The resulting amplicons are assessed for NHEJ mutations by next-generation sequencing (e.g., 454 pyrosequencing) or other methods for detecting relatively small indels (e.g., T7 endonuclease direct sequencing).

TALE nuclease activity also is assessed by transiently expressing TALE nuclease pairs in protoplasts. Methods for protoplast preparation and transformation are performed as described elsewhere (He et al., *Plant Cell Reports*, 14:192-196, 1994), with slight modifications. Briefly, leaves from 1 to 2 week old in vitro grown seedlings were used to prepare protoplasts. Seedlings (about 40) were cut above the roots and the leaves were sliced into small (~1-2 mm) sections. Sections were transferred to an enzyme solution containing macerozyme (0.75%) and cellulose (1.50%). The enzyme-plant mixture was incubated at 25° C. for 6-7 hours with shaking at 25 rpm. Following digestion, the solution was passed through a 100 micron filter and the protoplasts were pelleted by centrifugation at 100 g for 5 minutes. Cells were resuspended in W5 (154 mM sodium chloride, 125 mM calcium chloride, 5 mM potassium chloride, 2 mM MES, pH 5.7). The protoplast-W5 solution was then transferred to a tube containing 0.55 M sucrose. The solution was spun at 1000 g for 5 minutes. Protoplasts above the sucrose cushion were removed and transferred to a tube containing W5. Cells were counted, pelleted, and resuspended in MMG (0.4 M mannitol, 15 mM magnesium chloride, 4 mM MES, pH 5.7) to a concentration of 1,000,000 cells per mL. Cells were transformed using polyethylene glycol. DNA encoding TaSBEIIa TALE nuclease monomers was added to the transformation solution. 15 micrograms of each plasmid (30 micrograms total) was added to each reaction. Following transformation, cells were incubated at 25° C. for 48 hours. After incubation, cells were pelleted and DNA was isolated. This DNA was used as a template for PCR amplification using primers oNJB015 (GAGAGATAGCTGGATTAGGC-GATCG, SEQ ID NO:9) and oNJB016 (TTCAGTGGCC-CAAGAGCCAGC, SEQ ID NO:10) for amplifying the SBEIIa_T03 target site, or primers oNJB017 (TCAGATG-GATGTGCATTCTAGCAAG, SEQ ID NO:11) and oNJB018 (TCCCAGCATATTCTCAGACCA, SEQ ID NO:12) for amplifying the SBEIIa_T01 and T02 target sites.

To assess mutations introduced by the TaSBEIIa TALE nuclease pairs, PCR amplicons were deep sequenced using 454 pyrosequencing. Surprisingly, we observed that all TALE nuclease pairs created mutations within all three homoeoalleles, despite differences in target sequences. Specifically, the mutation frequency for TALE nuclease pair TaSBEIIa_T01 was 10.3% at the TaSBEIIa-A target, 6.21% at the TaSBEIIa-B target, and 11.87% at the TaSBEIIa-D target. The mutation frequency for TALE nuclease pair TaSBEIIa_T02 was 13.89% at the TaSBEIIa-A target, 4.93% at the TaSBEIIa-B target, and 5.03% at the TaSBEIIa-D target. The mutation frequency for TALE nuclease pair TaSBEIIa_T03 was 17.73% at the TaSBEIIa-A target, 20.57% at the TaSBEIIa-B target, and 34.58% at the TaSBEIIa-D target.

Mutations introduced by TALE nuclease pair TaSBEIIa_T01 within the SBEIIa-A allele are shown in SEQ ID NOS:13-515.

Mutations introduced by TALE nuclease pair TaSBEIIa_T01 within the SBEIIa-B allele are shown in SEQ ID NOS:516-695.

Mutations introduced by TALE nuclease pair TaSBEIIa_T01 within the SBEIIa-D allele are shown in SEQ ID NOS:696-955.

Mutations introduced by TALE nuclease pair TaSBEIIa_T02 within the SBEIIa-A allele are shown in SEQ ID NOS:956-1522.

Mutations introduced by TALE nuclease pair TaSBEIIa_T02 within the SBEIIa-B allele are shown in SEQ ID NOS:1523-1629.

Mutations introduced by TALE nuclease pair TaSBEIIa_T02 within the SBEIIa-D allele are shown in SEQ ID NOS:1630-1711.

Mutations introduced by TALE nuclease pair TaSBEIIa_T03 within the SBEIIa-A allele are shown in SEQ ID NOS:1712-2185.

Mutations introduced by TALE nuclease pair TaSBEIIa_T03 within the SBEIIa-B allele are shown in SEQ ID NOS:2186-3207.

Mutations introduced by TALE nuclease pair TaSBEIIa_T03 within the SBEIIa-D allele are shown in SEQ ID NOS:3208-5080.

To ensure reproducibility, the protoplast experiment was repeated and amplicons encompassing the TALE nuclease target sites were deep sequenced.

Mutations introduced by TALE nuclease pair TaSBEIIa_T01 within the SBEIIa-A or SBEIIa-B or SBEIIa-D alleles are shown in SEQ ID NOS:5083-7268. Mutations introduced by TALE nuclease pair TaSBEIIa_T02 within the SBEIIa-A or SBEIIa-B or SBEIIa-D alleles are shown in SEQ ID NOS:7269-8763. Mutations introduced by TALE nuclease pair TaSBEIIa_T03 within the SBEIIa-A or SBEIIa-B or SBEIIa-D alleles are shown in SEQ ID NOS: 8764-11889.

The majority of TALE nuclease-induced SBEIIa mutations in wheat cells included a deletion of the nucleotide at position 8 or position 9 of the 15 nucleotide TALE nuclease spacers. Specifically, TALE nuclease pair SBEIIa_T01 introduced mutations into the SBEIIa-A allele that comprised a deletion of the adenine nucleotide at position 1097 of SEQ ID NO:1. TALE nuclease pair SBEIIa_T01 introduced mutations into the SBEIIa-B allele that comprised a deletion of the adenine nucleotide at position 1376 of SEQ ID NO:5081. TALE nuclease pair SBEIIa_T01 introduced mutations into the SBEIIa-D allele that comprised a deletion of the adenine nucleotide at position 1370 of SEQ ID NO:5082. TALE nuclease pair SBEIIa_T02 introduced mutations into the SBEIIa-A allele that comprised a deletion of the guanine nucleotide at position 977 of SEQ ID NO:1. TALE nuclease pair SBEIIa_T02 introduced mutations into the SBEIIa-B allele that comprised a deletion of the guanine nucleotide at position 1256 of SEQ ID NO:5081. TALE nuclease pair SBEIIa_T02 introduced mutations into the SBEIIa-D allele that comprised a deletion of the guanine nucleotide at position 1250 of SEQ ID NO:5082. TALE nuclease pair SBEIIa_T03 introduced mutations into the SBEIIa-A allele that comprised a deletion of the guanine nucleotide at position 539 of SEQ ID NO:1. TALE nuclease pair SBEIIa_T03 introduced mutations into the SBEIIa-B allele that comprised a deletion of the guanine nucleotide at position 813 of SEQ ID NO:5081. TALE nuclease pair SBEIIa_T03 introduced mutations into the SBEIIa-D allele that comprised a deletion of the guanine nucleotide at position 811 of SEQ ID NO:5082.

Example 3—Regeneration of *T. aestivum* Lines with TALE Nuclease-Induced SBEIIa Mutations

*T. aestivum* lines were created with mutations in one or more SBEIIa alleles. Plant parts from *T. aestivum* (e.g., immature scutella, immature embryos, or embryogenic callus) were bombarded with one or more plasmids encoding TALE nuclease pairs and a plant stable marker. Alternatively, plant parts are transformed via *Agrobacterium* with one or more T-DNAs encoding TALE nuclease pairs and a plant selectable marker. Following transformation, plant parts were placed on selection and regeneration media. Materials and methods for regeneration were used as described elsewhere (Sparks et al., *Humana Press,* 478:71-92, 2009). The plasmid and T-DNA contained a selectable marker (e.g., bialaphos) for conferring herbicide tolerance and to facilitate selection of transgenic plants. Transformation efficiencies were monitored using a control plasmid or T-DNA plasmid containing pNos:YFP and pNos:Bar or pNos:PMI. To visualize cells or plants that have stably integrated this DNA into their genome, a fluorescent stereomicroscope was used to enable visualization of YFP expressed in cells transformed with pNos:YFP.

Thirty-four experiments (TABLE 1) were carried out using biolistics as the DNA delivery method. Wheat scutella were isolated from immature kernels and used for transformation and regeneration of complete transgenic plants. More than 3,600 scutella were isolated and transformed with plasmids encoding SBEIIa_T03 TALE nucleases (pCLS27224, pCLS27225).

T0 whole plants regenerated on selection were transferred to soil. After about a 1-week acclimation period, DNA was isolated from leaves and screened for the presence of integrated plasmid DNA. Twenty transgenic plants were identified, resulting in a transformation efficiency of 0.55%.

The twenty transgenic plants were then advanced to genotypic screening for mutations at the SBEIIa_T03 target site by PCR, cloning, and Sanger sequencing. Primers specific for each SBEIIa gene were used to amplify the SBEIIa_T03 target sites. Primers that were used to amplify the SBEIIa_T03 target site in the A genome were oJG029 (CGGACTGCTGCCGCGAT; SEQ ID NO:11902) and oJG030 (TGTAGCCATCAATTATACATCTACG; SEQ ID NO:11903). Primers that were used to amplify the SBEIIa_T03 target site in the B genome were oJG031 (GGCGGACTGCTGCGATC; SEQ ID NO:11904) and oJG032 (CAATTGTAGCCAGCAATTATACATA; SEQ ID NO:11905). Primers that were used to amplify the SBEIIa_T03 target site in the D genome were SBEIIa-D-L1 (TTTTCCCCGCGGGGAAATGCG; SEQ ID NO:11906) and oNJB033 (TCCACCTTCATGTTGGTCAATAGCAGC; SEQ ID NO:11907). The resulting amplicons were cloned and sequenced.

Four T0 plants were identified with mutations in one, two, or all three SBEIIa genes. These T0 plants are referred to as Ta125-2, Ta128-1, Ta137-1, and Ta139-1.

Ta125-2 contained mutations in the SBEIIa-A, SBEIIb-B, and SBEIIa-D genes (FIG. 4). The mutations identified in the SBEIIa-A gene were a 2 bp insertion (SEQ ID NO:11909) and a 23 bp deletion (SEQ ID NO:11910). The mutations identified in the SBEIIa-B gene were a 4 bp deletion (SEQ ID NO:11912) and a 20 bp deletion (SEQ ID NO:11913). The mutations identified in the SBEIIa-D gene were a 4 bp deletion (SEQ ID NO:11915) and a 12 bp deletion (SEQ ID NO:11916).

Ta128-1 contained mutations in the SBEIIb-B and SBEIIa-D genes (FIG. 5). The mutations identified in the SBEIIa-B gene were a 1 bp insertion (SEQ ID NO:11917) and a 1 bp deletion (SEQ ID NO:11918). The mutations identified in the SBEIIa-D gene were a 21 bp deletion (SEQ ID NO:11919) and an 890 bp deletion (SEQ ID NO:11920).

Ta137-1 contained mutations in the SBEIIa-A, SBEIIb-B, and SBEIIa-D genes (FIGS. 6A and 6B). The mutations identified in the SBEIIa-A gene were a 4 bp deletion (SEQ ID NO:11921), a 7 bp deletion (SEQ ID NO:11922), a 13 bp deletion (SEQ ID NO:11923), and a 167 bp deletion (SEQ ID NO:11924). The mutation identified in the SBEIIa-B gene was a 17 bp deletion (SEQ ID NO:11925). The mutations identified in the SBEIIa-D gene were a 6 bp deletion (SEQ ID NO:11926), a 10 bp deletion (SEQ ID NO:11927), a 13 bp deletion (SEQ ID NO:11928), a 14 bp deletion (SEQ ID NO:11929), and a 15 bp deletion (SEQ ID NO:11930).

Ta139-1 contained mutations in the SBEIIa-A, SBEIIb-B, and SBEIIa-D genes (FIG. 7). The mutation identified in the SBEIIa-A gene was a 4 bp deletion (SEQ ID NO:11931). The mutations identified in the SBEIIa-B gene were a 4 bp deletion (SEQ ID NO:11932), a 10 bp deletion (SEQ ID NO:11933), and a 22 bp deletion (SEQ ID NO:11934). The mutations identified in the SBEIIa-D gene were an 11 bp deletion (SEQ ID NO:11935) and a 17 bp deletion (SEQ ID NO:11936).

To generate wheat lines that stably transmitted mutations to progeny, the line Ta125-2 was selfed and the progeny were screened for homozygous mutations. After selfing line Ta125-2 once, a mutant was generated with the genotype -23/-23, -4/-4, -12/-12, corresponding to the SBEIIa-A, SBEIIa-B, SBEIIa-D alleles, respectively. The resulting plant was named Ta125-2-14, and contained the mutations shown in SEQ ID NOs:11910, 11912 and 11916 (FIG. 8).

After selfing line Ta125-2 three times, two mutants were generated with homozygous mutations that were predicted to result in frameshifts. The first line, which is named Ta125-2-44-1-1a (-23/-23, -4/-4, -4/-4), has a genotype of -23/-23, -4/-4, -4/-4, corresponding to the SBEIIa-A, SBEIIa-B, SBEIIa-D alleles, respectively. The resulting plant [Ta125-2-44-1-1a (-23/-23, -4/-4, -4/-4)] contained the mutations shown in SEQ ID NOs:11910, 11912, and 11915 (FIG. 9). The second line, which is named Ta125-2-44-1-2a (-23/-23, -20/-20, -4/-4), has a genotype of -23/-23, -20/-20-4/-4, corresponding to the SBEIIa-A, SBEIIa-B, SBEIIa-D alleles, respectively. The resulting plant [Ta125-2-44-1-2a (-23/-23, -20/-20, -4/-4)] contained the mutations shown in SEQ ID NOs: 11910, 11913 and 11915 (FIG. 10).

Multiplex PCR was performed to detect integration of DNA from the vectors used for transformation. The PCR failed to amplify sequence from the transformed vectors in six lines that are the progeny of Ta125-2-44 (which includes Ta125-2-44-1-1a and Ta125-2-44-1-2a), thereby indicating that the transgene had segregated away.

Example 4—Assessing Phenotypes in Modified *T. aestivum* Plants

*T. aestivum* plants containing mutations within SBEIIa alleles were assessed for total protein and starch content, percent of amylose and amylopectin in total starch, and total resistant starch and dietary fiber. Composition analysis was performed in plants grown in greenhouse conditions and field conditions.

Protein content was determined following Official Methods AACC 46-30 and AOAC 992.15 (Official Methods of Analysis of AOAC INTERNATIONAL (2005) 18th Ed., AOAC International, Gaithersburg, MD). Total starch and resistant starch were calculated following Official Method AOAC 2002.02 (Official Methods of Analysis of AOAC INTERNATIONAL, supra). To determine the amylose/amylopectin ratio, the Amylose Kit (K-AMYL) from Megazyme (Bray, County Wicklow, Ireland) was used. As an alternative method for analyzing amylose content, iodine binding and/or the concanavalin A method are performed as described elsewhere (Zhu et al., *Cereal Chem*, 85:51-58, 2008; and Gibson et al., *J. Cereal Sci*, 25:111-119, 1997). Total dietary fiber was calculated following Official Methods AOAC 2009.01 and 2011.25 (Official Methods of Analysis of AOAC INTERNATIONAL, supra).

Three to four biological repetitions and one to three technical repetitions were used to determine the content of protein, starch, amylose, amylopectin, resistant starch, and dietary fiber in white flour extracted from the following groups: (1) Ta125-2-44-1a (-23/-23, -4/-4, -4/-4), (2) Ta125-2-44-2a (-23/-23, -20/-20, -4/-4), (3) Ta125-2-14 (-23/-23, -4/-4, -12/-12), and (4) wild type control.

Results obtained from plants grown in greenhouse conditions showed a significant increase in total protein in the complete knockout and partial knockout lines, compared to wild type controls, whereas total starch was significantly reduced. Amylose content was higher in the complete knockout lines than in wild type control—from 26.5% to 49.9% and 50.3%, respectively in Ta125-2-44-1-1a (-23/-23,-4/-4,-4/-4) and Ta125-2-44-1-2a (-23/-23,-20/-20,-4/-4). The partial knockout showed an amylose content similar to WT (TABLE 1). Similar results were obtained from plants grown in field conditions, with complete knockout and partial knockout lines showing higher protein, lower starch, and complete knockout lines showing higher amylose content (TABLE 2).

Resistant starch and total dietary fiber levels were found to be significantly higher in the complete knockout samples, but not in the partial knockout samples. Complete knockout lines grown in greenhouse conditions showed a 7- to 8-fold increase in resistant starch in white flour as compared to wild type control—from 2.2% to 25.9% and 28.8%, respectively in Ta125-2-44-1-1a (-23/-23,-4/-4,-4/-4) and Ta125-2-44-1-2a (-23/-23, -20/-20,-4/-4) (TABLE 3). Total dietary fiber in white flour was significantly increased in the complete knockout lines compared to the wild type control, both in plants grown in greenhouse and in plants grown in field conditions. Complete knockout lines grown in the field showed up to a 6.2-fold increase in total dietary fiber content (TABLES 3 and 4). Dietary fiber was quantified in whole wheat flour samples from plants grown in greenhouse conditions, showing a 2-fold increase compared to the wild type control—from 18% in the wild type control to 34.65% and 32.74% in Ta125-2-44-1-1a (-23/-23, -4/-4,-4/-4) and Ta125-2-44-1-2a (-23/-23,-20/-20,-4/-4), respectively (TABLE 5).

Example 5—Assessing Morphology in Complete Knockout *T. aestivum* Plants

*T. aestivum* plants containing complete knockout mutations within SBEIIa alleles were assessed for morphological characteristics. One to three measurements were taken for three independent plants to quantify the number of seeds per spike, and to determine plant height. Germination tests were performed as described in the "AOSA Rules for Testing Seeds: Volume 1. Principles and Procedures," pp. 6-63, 2017. Four independent repetitions with 400 seeds each were done for each of the complete knockout mutants and wild type controls.

Figure 11A:
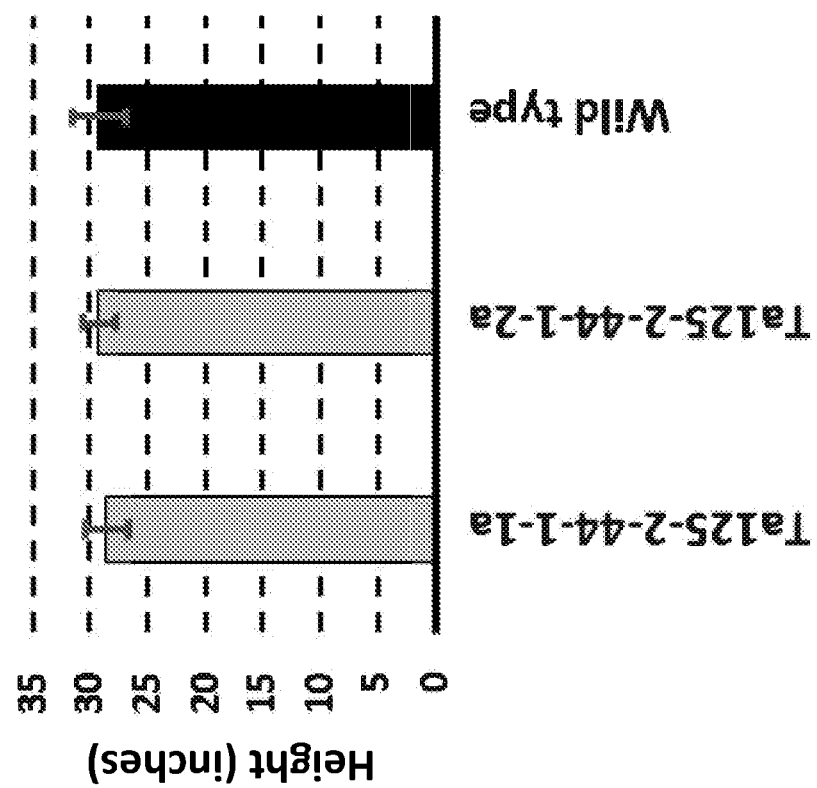

Plant height and number of seeds per spike were comparable in the mutant lines and the wild type controls (FIGS. 11A and 11B). Germination was significantly lower in the Ta125-2-44-1-2a line (94.5%) compared to the wild type control (98%) at both the P=0.05 and P=0.01 levels, while mutant line Ta125-2-44-1-1a demonstrated germination efficiency that was comparable to that of the wild type control (FIG. 11C).

TABLE 1

Composition analysis (protein %, starch %, and amylose % and amylopectin % of total starch) in white flour samples grown in greenhouse conditions. Data are expressed on a dry basis.

| Sample | Total Protein (%) | Standard Deviation (%) | Total Starch (%) | Standard Deviation (%) | Amylose (% of Total Starch) | Standard Deviation (%) | Amylopectin (% of Total Starch) | Standard Deviation (%) |
|---|---|---|---|---|---|---|---|---|
| Ta125-2-44-1-1a (−23/−23,−4/−4,−4/−4) | 21.2 | 0.9 | 58.1 | 1.4 | 50.3 | 1.4 | 49.7 | 1.4 |
| Ta125-2-44-1-2a (−23/−23,−20/−20,−4/−4) | 21.9 | 0.4 | 56.9 | 0.5 | 49.9 | 2.7 | 50.1 | 2.7 |

TABLE 1-continued

Composition analysis (protein %, starch %, and amylose % and amylopectin % of total starch) in white flour samples grown in greenhouse conditions. Data are expressed on a dry basis.

| Sample | Total Protein (%) | Standard Deviation (%) | Total Starch (%) | Standard Deviation (%) | Amylose (% of Total Starch) | Standard Deviation (%) | Amylopectin (% of Total Starch) | Standard Deviation (%) |
|---|---|---|---|---|---|---|---|---|
| Ta125-2-14 (−23/−23,−4/−4,−12/−12) | 22.5 | N/A | 60.0 | N/A | 24.3 | N/A | 75.7 | N/A |
| Wild type control | 18.7 | 1.9 | 63.0 | 1.1 | 26.5 | 0.4 | 73.5 | 0.4 |

TABLE 2

Composition analysis (protein %, starch %, and amylose % and amylopectin % of total starch) in white flour samples grown in field conditions. Data expressed in a dry basis.

| Sample | Total Protein (%) | Standard Deviation (%) | Total Starch (%) | Standard Deviation (%) | Amylose (% of Total Starch) | Standard Deviation (%) | Amylopectin (% of Total Starch) | Standard Deviation (%) |
|---|---|---|---|---|---|---|---|---|
| Ta125-2-44-1-1a (−23/−23,−4/−4,−4/−4) | 19.1% | 0.1% | 61.7% | N/A | 47.7% | 0.5% | 52.3% | 0.5% |
| Ta125-2-44-1-2a (−23/−23,−20/−20,−4/−4) | 18.4% | 0.3% | 61.7% | 0.3% | 49.9% | 2.6% | 50.1% | 2.6% |
| Ta125-2-14 (−23/−23,−4/−4,−12/−12) | N/A | N/A | N/A | N/A | N/A | N/A | N/A | N/A |
| Wild type control | 16.3% | 0.2% | 67.9% | 0.7% | 25.4% | 1.2% | 74.6% | 1.2% |

TABLE 3

Composition analysis (resistant starch % and total dietary fiber %) in white flour samples grown in greenhouse conditions. Data expressed in a dry basis.

| Sample | Resistant Starch (%) | Standard Deviation (%) | Fold increase | Total Dietary Fiber (%) | Standard Deviation (%) | Fold increase |
|---|---|---|---|---|---|---|
| Ta125-2-44-1-1a (−23/−23,−4/−4,−4/−4) | 17.8 | 3.3 | 7.9 | 16.9 | 0.8 | 2.6 |
| Ta125-2-44-1-2a (−23/−23,−20/−20,−4/−4) | 15.5 | 0.7 | 6.9 | 15.7 | 1.1 | 2.5 |
| Ta125-2-14 (−23/−23,−4/−4,−12/−12) | 2.2 | N/A | 1.0 | 5.4 | N/A | 0.9 |
| Wild type control | 2.2 | 0.0 | 1.0 | 6.4 | 0.3 | 1.0 |

TABLE 4

Total dietary fiber (%) in white flour samples grown in field conditions. Data expressed in a dry basis.

| Sample | Total Dietary Fiber (%) | Standard Deviation (%) | Fold increase |
|---|---|---|---|
| Ta125-2-44-1-1a (−23/−23,−4/−4,−4/−4) | 28.8% | N/A | 6.2 |
| Ta125-2-44-1-2a (−23/−23,−20/−20,−4/−4) | 25.9% | 1.8% | 5.6 |
| Ta125-2-14 (−23/−23,−4/−4,−12/−12) | N/A | N/A | N/A |
| Wild type control | 4.7% | 0.2% | N/A |

TABLE 5

Total dietary fiber (%) in whole flour samples grown in greenhouse conditions. Data expressed in a dry basis.

| Sample | Total Dietary Fiber (%) | Standard Deviation (%) | Fold increase |
|---|---|---|---|
| Ta125-2-44-1-1a (−23/−23,−4/−4,−4/−4) | 34.65 | 0.05 | 1.92 |
| Ta125-2-44-1-2a (−23/−23,−20/−20,−4/−4) | 32.74 | 2.20 | 1.82 |
| Wild type control | 18.02 | 0.90 | N/A |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

wild-type, wherein the plant, plant part, or plant cell contains an A, B, and D genome and the mutations are homozygous mutations in the SBEIIa-A, B and D alleles.

SEQUENCE LISTING

The patent contains a lengthy sequence listing. A copy of the sequence listing is available in electronic form from the USPTO web site (https://seqdata.uspto.gov/?pageRequest=docDetail&DocID=US12012607B2). An electronic copy of the sequence listing will also be available from the USPTO upon request and payment of the fee set forth in 37 CFR 1.19(b)(3).

What is claimed is:

1. A hexaploid *Triticum* plant, plant part, or plant cell comprising at least three deletion or insertion mutations induced by contact with a transcription activator-like effector (TALE) nuclease configured to bind a nucleic acid sequence as set forth in SEQ ID NO: 8,
wherein the at least three deletion or insertion mutations are within the binding site of the TALE nuclease in at least three starch branching enzyme IIa (SBEIIa) alleles endogenous to the plant, plant part, or plant cell, in each genome,
wherein each starch branching enzyme IIb (SBEIIb) allele of the hexaploid *Triticum* plant, plant part, or plant cell is a wild-type SBEIIb allele, and wherein the *Triticum* plant, plant part or plant cell has increased levels of dietary fiber as compared to a control hexaploid *Triticum* plant in which the SBEIIa alleles have not been mutated, and
wherein the mutant SBEIIa alleles comprise the sequences set forth in SEQ ID NO:11910, 11912, and 11915, respectively, or the sequences set forth in SEQ ID NO:11910, 11913, and 11915, respectively, wherein the plant, plant part, or plant cell contains an A, B, and D genome and the mutations are homozygous mutations in the SBEIIa-A, B and D alleles.

2. The plant, plant part, or plant cell of claim 1, wherein the at least three induced deletion or insertion mutations comprise a deletion of one or more nucleotide base pairs in each of the at least three SBEIIa alleles.

3. The plant, plant part, or plant cell of claim 1, wherein the at least three induced deletion or insertion mutations comprise an insertion of one or more nucleotide base pairs endogenous to the plant, plant part, or plant cell in each of the at least three SBEIIa alleles.

4. The plant, plant part, or plant cell of claim 1, wherein every endogenous SBEIIa allele comprises the deletion or insertion induced by the TALE nuclease configured to bind to SEQ ID NO: 8.

5. A *Triticum* plant, plant part, or plant cell comprising mutations within three starch branching enzyme IIa (SBEIIa) homoeoalleles endogenous to the plant, plant part, or plant cell, wherein the mutant SBEIIa homoeoalleles comprise the sequences set forth in SEQ ID NO:11910, 11912, and 11915, respectively, or the sequences set forth in SEQ ID NO:11910, 11913, and 11915, respectively, and wherein the *Triticum* plant, plant part or plant cell has increased levels of dietary fiber as compared to a control hexaploid *Triticum* plant in which the SBEIIa alleles are wild-type, wherein the plant, plant part, or plant cell contains an A, B, and D genome and the mutations are homozygous mutations in the SBEIIa-A, B and D alleles.

6. The plant, plant part, or plant cell of claim 1, wherein each of the genomes exhibit removal of an endogenous nucleic acid of the at least three SBEIIa alleles and do not include any exogenous nucleic acid in the at least three SBEIIa alleles.

7. The plant, plant part, or plant cell of claim 1, wherein the plant part is grain.

8. The plant, plant part, or plant cell of claim 7, wherein the grain is milled, ground, pearled, rolled, kibbled, parboiled, or cracked grain.

9. The plant, plant part, or plant cell of claim 1, wherein the hexaploid *Triticum* plant, plant part, or plant cell is of the species *Triticum aestivum*.

10. A method for generating a *Triticum* plant that has increased levels of dietary fiber, wherein the method comprises:
(a) contacting a hexaploid *Triticum* plant cell or plant part comprising functional SBEII alleles with a TALE nuclease configured to bind to a nucleic acid sequence as set forth in SEQ ID NO: 8;
(b) selecting from the plant cell or plant part a plant cell or plant part in which at least one SBEIIa allele in each genome of the plant cell or plant part comprises a deletion or insertion mutation within the binding site of the TALE nuclease and each SBEIIb allele is a wild-type SBEIIb allele; and
(c) growing the selected plant cell or plant part into a *Triticum* plant, wherein the *Triticum* plant has increased levels of dietary fiber as compared to a control hexaploid *Triticum* plant in which the SBEIIa alleles have not been mutated, wherein the mutant SBEIIa alleles comprise the sequences set forth in SEQ ID NO:11910, 11912, and 11915, respectively, or the sequences set forth in SEQ ID NO:11910, 11913, and 11915, respectively, and wherein the selected plant cell or plant part contains an A, B, and D genome and the mutations are homozygous mutations in the SBEIIa-A, B and D alleles.

11. The method of claim 10, wherein the hexaploid *Triticum* plant cell is a protoplast.

12. The method of claim 11, wherein the contacting comprises transforming the protoplast with a nucleic acid encoding the TALE nuclease.

13. The method of claim 12, wherein the nucleic acid is an mRNA.

14. The method of claim 12, wherein the nucleic acid is contained within a vector.

15. The method of claim 11, further comprising culturing the protoplast to generate a plant line.

16. The method of claim 11, further comprising isolating genomic DNA comprising at least a portion of the at least one SBEIIa allele from the protoplast.

17. The method of claim 10, wherein the hexaploid *Triticum* plant part is an immature embryo, embryogenic callus, or scutella.

18. The method of claim 17, wherein the contacting comprises transforming the immature embryo, embryogenic callus, or scutella with a nucleic acid encoding the TALE nuclease.

19. The method of claim 18, wherein the transforming comprises *Agrobacterium*-mediated transformation or biolistics.

20. The method of claim 17, further comprising culturing the immature embryo, embryogenic callus, or scutella to generate a plant line.

21. The method of claim 17, further comprising isolating genomic DNA comprising at least a portion of the at least one SBEIIa allele from the immature embryo, embryogenic callus, or scutella.

22. The method of claim 10, wherein the *Triticum* plant cell or plant part is of the species *Triticum aestivum*.

23. The plant, plant part, or plant cell of claim 1, wherein the plant, plant part, or plant cell comprises an A, B and D genome and the SBEIIa-A allele comprises a deletion at position 539 of SEQ ID NO:1.

24. The plant, plant part, or plant cell of claim 23, wherein the plant, plant part, or plant cell further comprises a SBEIIa-B allele comprising a deletion at position 813 of SEQ ID NO: 5081.

25. The plant, plant part, or plant cell of claim 23, wherein the plant, plant part, or plant cell further comprises a SBEIIa-D allele comprising a deletion at position 811 of SEQ ID NO: 5082.

26. The plant, plant part, or plant cell of claim 25, wherein the plant, plant part, or plant cell further comprises a SBEIIa-B allele comprising a deletion at position 813 of SEQ ID NO: 5081.

27. The method of claim 10, further comprising selfing the grown *Triticum* plant to generate a plant line homozygous for the mutant SBEIIa alleles.

28. The plant, plant part, or plant cell of claim 7, wherein the grain has a starch content that includes at least 40% (w/w) amylose.

29. The plant, plant part, or plant cell of claim 7, wherein the grain has an increased amount of total protein compared with a control grain of a hexaploid *Triticum* plant in which the SBEIIa alleles have not been mutated.

* * * * *